(12) United States Patent
Wang

(10) Patent No.: US 8,900,846 B2
(45) Date of Patent: *Dec. 2, 2014

(54) NUCLEIC ACID MODIFYING ENZYMES

(71) Applicant: Bio-Rad Laboratories, Inc., Hercules, CA (US)

(72) Inventor: Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,044

(22) Filed: Oct. 18, 2013

(65) Prior Publication Data

US 2014/0038237 A1  Feb. 6, 2014

Related U.S. Application Data

(63) Continuation of application No. 13/850,048, filed on Mar. 25, 2013, which is a continuation of application No. 13/047,638, filed on Mar. 14, 2011, now Pat. No. 8,415,129, which is a continuation of application No. 10/256,705, filed on Sep. 27, 2002, now Pat. No. 7,919,296, which is a continuation of application No. 09/640,958, filed on Aug. 16, 2000, now Pat. No. 6,627,424.

(60) Provisional application No. 60/207,567, filed on May 26, 2000.

(51) Int. Cl.
| | |
|---|---|
| *C12N 9/12* | (2006.01) |
| *C12P 19/34* | (2006.01) |
| *C12N 9/96* | (2006.01) |
| *C07K 19/00* | (2006.01) |
| *C07K 14/00* | (2006.01) |

(52) U.S. Cl.
CPC .............. *C07K 14/001* (2013.01); *C12P 19/34* (2013.01); *C12N 9/96* (2013.01); *C12N 9/1252* (2013.01); *C07K 19/00* (2013.01)
USPC ........... 435/194; 435/183; 435/91.1; 530/350

(58) Field of Classification Search
USPC .......................... 435/183, 194, 69.1; 530/350
See application file for complete search history.

(56) References Cited

U.S. PATENT DOCUMENTS

| | | | |
|---|---|---|---|
| 5,474,911 A | 12/1995 | Pontius | |
| 5,972,603 A | 10/1999 | Bedford et al. | |
| 6,228,628 B1 | 5/2001 | Gelfand et al. | |
| 6,607,883 B1 | 8/2003 | Frey et al. | |
| 6,627,424 B1 * | 9/2003 | Wang | ............................ 435/194 |

FOREIGN PATENT DOCUMENTS

| | | |
|---|---|---|
| DE | 198 40 771 A1 | 2/2000 |
| EP | 1 925 669 A1 | 5/2008 |

OTHER PUBLICATIONS

Supplementary Partial European Search Report from EP Application No. 01941707, dated Nov. 12, 2004 (5 pages).
Written Opinion from International Application No. PCT/US01/17492, dated May 20, 2002 (2 pages).
Baumann et al., "Solution structure and DNA-binding properties of a thermostable protein from the Archaeon *Sulfolobus solfataricus*" *Structural Biology* (1994) 1( 11): 808-819.
Bedford et al., "The Thioredoxin Binding Domain of Bacteriophage T7 DNA Polymerase Confers Processivity on *Escherichia coli* DNA Polymerase I," *Proc. Natl. Acad. Sci. USA* (Jan. 1997) 94: 479-484.
Cann et al., "Functional interactions of a homolog of proliferating cell nuclear antigen with DNA polymerases in Archaea," *Journal of Bacteriology* (1999) 181(21): 6591-6599.
Carrodeguas et al., "The Accessory Subunit of *Xenopus laevis* Mitochondrial DNA Polymerase ÿ Increases Processivity of the Catalytic Subunit of Human DNA Polymerase ÿ and is Related to Class II Aminoacyl-tRNA Synthetases," *Molecular and Cellular Biology* (Jun. 1999) 19(6): 4039-4046.
Choli et al., "Isolation, characterization and micro sequence analysis, of a small basic methylated DNA-binding protein from the Archaebacterial, *Sulfolobus solfataricus*," *Biochimica et Biophysica Acta* (1988) 950: 193-203.
Consonni et al., "A Single-Point Mutation in the Extreme Heat- and Pressure-Resistant Sso7d Protein from *Sulfolobus solfataricus* Leads to a Major Rearrangement of the Hydrophobic Core," *Biochemistry* (1999) 38: 12709-12717.
De Felice et al., "Two DNA polymerase sliding clamps from the thermophilic Archaeon, *Sulfolobus solfataricus*," *Molecular Biology* (1999) 291: 47-57.
Gao et al., "The crystal structure of the hyperthermophile chromosomal protein Sso7d bound to DNA," *Nature Structural Biology* (1998) 5(9): 782-786.
Lim et al., "The Mitochondrial p55 Accessory Subunit of Human DNA Polymerase γ Enhances DNA Binding, Promotes Processive DNA Synthesis, and Confers N-Ethylmaleimide Resistance" *J. Biological Chemistry* (Dec. 1999) 274(53): 38197-38203.
McAfee et al., "Gene cloning, expression, and characterization of the Sac7 proteins from the hyperthermophile *Sulfolobus acidocaldarius*" *Biochemistry* (1995) 34: 10063-10077.

(Continued)

*Primary Examiner* — Richard Hutson
(74) *Attorney, Agent, or Firm* — Kilpatrick Townsend & Stockton LLP

(57) ABSTRACT

This invention provides for an improved generation of novel nucleic acid modifying enzymes. The improvement is the fusion of a sequence-non-specific nucleic-acid-binding domain to the enzyme in a manner that enhances the ability of the enzyme to bind and catalytically modify the nucleic acid.

16 Claims, 3 Drawing Sheets

(56) References Cited

OTHER PUBLICATIONS

Motz et al., "Elucidation of an archaeal replication protein network to generate enhanced PCR enzymes," *Journal Biological Chemistry* (May 2002) 277(18): 16179-16188.

Ngo et al., "Computational Complexity, Protein Structure Prediction, and the Levinthal Paradox," in The Protein Folding Problem and Tertiary Structure Prediction, 1994, Merz et al. (ed.), Birkhauser, Boston, MA, pp. 433 and 492-495.

Pavlov et al., "Helix-hairpin-helix motifs confer salt resistance and processivity on chimeric DNA polymerases" *Proc. Natl. Acad. Sci. USA* (Oct. 2002) 99(21): 13510-13515.

Robinson et al., "The hyperthermophile chromosomal protein Sac7d sharply kinks DNA"; *Nature* (Mar. 1998) 392: 202-205.

Sandman et al., "Histone-encoding genes from *Pyrococcus*: evidence for members of the HMf family of archaeal histones in a non-methanogenic Archeaon," *Gene* (1994) 150: 207-208.

Sandman et al., "HMf, a DNA-binding protein isolated from the hyperthermophilic archaeon *Methanothermus fervidus*, is most closely related to histones," *Proc. Natl. Acad. Sci. USA* (Aug. 1990) 87: 5788-5791.

Shamoo and Steitz, "Building a replisome from interacting pieces: Sliding clamp complexed to a peptide from DNA polymerase and a polymerase editing complex," *Cell* (1999) 99: 155-166.

Shehi et al., "Thermal Stability and DNA Binding Activity of a Variant Form of the Sso7d Protein from the Archeon *Sulfolobus solfataricus* Truncated at Leucine 54," *Biochemistry* (2003) 42: 8362-8368.

Starich et al., "NMR structure of HMfB from the hyperthermophile, *Methanothermus fervidus*, confirms that this archaeal protein is a histone," *J. Molec. Biol.* (1999) 255: 187-203.

Wang, et al., "A novel strategy to engineer DNA polymerases for enhanced processivity and improved performance in vitro"; *Nucleic Acids Research* (2004) 32(3): 1197-1207.

Weisshart et al., "Herpes Simplex Virus Processivity Factor UL42 Imparts Increased DNA-Binding Specificity to the Viral DNA Polymerase and Decreased Dissociation from Primer-Template without Reducing the Elongation Rate," *Journal of Virology* (Jan. 1999) 73(1): 55-66.

Zhang et al., "Expression and psysicochemical characterization of human proliferating cell nuclear antigen," *Biochemistry* (1995) 34: 10703-10712.

* cited by examiner

SEQUENCE LISTING

<160> NUMBER OF SEQ ID NOS: 17

<210> SEQ ID NO 1
<211> LENGTH: 189
<212> TYPE: DNA

<213> ORGANISM: Artificial Sequence
<220> FEATURE:
<223> OTHER INFORMATION: Description of Artificial Sequence:synthetic
      Sulfolobus solfataricus Sso7d gene
<220> FEATURE:
<221> NAME/KEY: CDS
<222> LOCATION: (1)..(189)
<223> OTHER INFORMATION: Sso7d

<400> SEQUENCE: 1

```
gcaaccgtaa agttcaagta caaaggcgaa gaaaaagagg tagacatctc caagatcaag      60
aaagtatggc gtgtgggcaa gatgatctcc ttcacctacg acgagggcgg tggcaagacc     120
ggccgtggtg cggtaagcga aaaggacgcg ccgaaggagc tgctgcagat gctggagaag     180
cagaaaaag                                                             189
```

<210> SEQ ID NO 2
<211> LENGTH: 63
<212> TYPE: PRT
<213> ORGANISM: Artificial Sequence
<220> FEATURE:
<223> OTHER INFORMATION: Description of Artificial Sequence:synthetic
      Sulfolobus solfataricus Sso7d gene amino acid
      sequence
<220> FEATURE:
<223> OTHER INFORMATION: Sso7d

<400> SEQUENCE: 2

```
Ala Thr Val Lys Phe Lys Tyr Lys Gly Glu Glu Lys Glu Val Asp Ile
  1               5                  10                  15

Ser Lys Ile Lys Lys Val Trp Arg Val Gly Lys Met Ile Ser Phe Thr
             20                  25                  30

Tyr Asp Glu Gly Gly Gly Lys Thr Gly Arg Gly Ala Val Ser Glu Lys
         35                  40                  45

Asp Ala Pro Lys Glu Leu Leu Gln Met Leu Glu Lys Gln Lys Lys
     50                  55                  60
```

<210> SEQ ID NO 3
<211> LENGTH: 1899
<212> TYPE: DNA
<213> ORGANISM: Artificial Sequence
<220> FEATURE:
<223> OTHER INFORMATION: Description of Artificial Sequence:Sso7d fused
      to N terminus of deltaTaq, Sso7d-deltaTaq fusion
      protein
<220> FEATURE:
<221> NAME/KEY: CDS
<222> LOCATION: (1)..(1899)
<223> OTHER INFORMATION: Sso7d-deltaTaq fusion protein

<400> SEQUENCE: 3

```
atgattacga attcgagcgc aaccgtaaag ttcaagtaca aggcgaaga aaaagaggta       60 gacatctcca agatcaagaa agtatggcgt gtgggcaaga tgatctcctt cacctacgac    120
gagggcggtg gcaagaccgg ccgtggtgcg gtaagcgaaa aggacgcgcc gaaggagctg    180
ctgcagatgc tggagaagca gaaaaagggc ggcggtgtca ctagtcccaa ggccctggag    240
gaggccccct ggccccccgc cggaaggggcc ttcgtgggct tgtgctttc ccgcaaggag    300 cccatgtggg ccgatcttct ggccctggcc gccgccaggg gggccgggt ccaccggcc     360 cccgagcctt ataaagccct cagggacctg aaggaggcgc gggggcttct cgccaaagac    420
ctgagcgttc tggccctgag ggaaggcctt ggcctcccgc cggcgacga ccccatgctc     480 ctcgcctacc tcctggaccc ttccaacacc accccgagg gggtggcccg gcgctacggc    540
```

-continued

```
ggggagtgga cggaggaggc gggggagcgg gccgcccttt ccgagaggct cttcgccaac    600
ctgtggggga ggcttgaggg ggaggagagg ctcctttggc tttaccggga ggtggagagg    660
cccctttccg ctgtcctggc ccacatggag gccacggggg tgcgcctgga cgtggcctat    720
ctcagggcct tgtccctgga ggtggccgag gagatcgccc gcctcgaggc cgaggtcttc    780
cgcctggccg gccaccccct caacctcaac tcccgggacc agctggaaag ggtcctcttt    840
gacgagctag ggcttccgc catcggcaag acggagaaga ccggcaagcg ctccaccagc    900
gccgccgtcc tggaggccct ccgcgaggcc cacccatcg tggagaagat cctgcagtac    960
cgggagctca ccaagctgaa gagcacctac attgaccct gccggacct catccacccc   1020
aggacgggcc gcctccacac ccgcttcaac cagacggcca cggccacggg caggctaagt   1080
agctccgatc ccaacctcca gaacatcccc gtccgcaccc cgcttgggca gaggatccgc   1140
cgggccttca tcgccgagga ggggtggcta ttggtggccc tggactatag ccagatagag   1200
ctcagggtgc tggcccacct ctccggcgac gagaacctga tccgggtctt ccaggagggg   1260
cgggacatcc acacgagac cgccagctgg atgttcggcg tcccccggga ggccgtggac   1320
cccctgatgc gccgggcggc caagaccatc aacttcgggg tcctctacgg catgtcggcc   1380
caccgcctct cccaggagct agccatccct tacgaggagg cccaggcctt cattgagcgc   1440
tactttcaga gcttccccaa ggtgcgggcc tggattgaga agaccctgga ggagggcagg   1500
aggcgggggt acgtggagac cctcttcggc cgccgccgct acgtgccaga cctagaggcc   1560
cgggtgaaga gcgtgcggga ggcggccgag cgcatggcct tcaacatgcc cgtccagggc   1620
accgccgccg acctcatgaa gctggctatg gtgaagctct ccccaggct ggaggaaatg   1680
ggggccagga tgctccttca ggtccacgac gagctggtcc tcgaggcccc aaaagagagg   1740
gcggaggccg tggcccggct ggccaaggag gtcatggagg gggtgtatcc cctggccgtg   1800
cccctggagg tggaggtggg gataggggag gactggctct ccgccaagga gggcattgat   1860
ggccgcggcg gaggcgggca tcatcatcat catcattaa                           1899
```

<210> SEQ ID NO 4
<211> LENGTH: 632
<212> TYPE: PRT
<213> ORGANISM: Artificial Sequence
<220> FEATURE:
<223> OTHER INFORMATION: Description of Artificial Sequence:Sso7d fused
      to N terminus of deltaTaq, Sso7d-deltaTaq fusion
      protein
<220> FEATURE:
<223> OTHER INFORMATION: Sso7d-deltaTaq fusion protein

<400> SEQUENCE: 4

```
Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Trp Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Val Thr Ser Pro Lys Ala Leu Glu
 65                  70                  75                  80

Glu Ala Pro Trp Pro Pro Pro Glu Gly Ala Phe Val Gly Phe Val Leu
                 85                  90                  95

Ser Arg Lys Glu Pro Met Trp Ala Asp Leu Leu Ala Leu Ala Ala Ala
```

```
              100                 105                 110
Arg Gly Gly Arg Val His Arg Ala Pro Glu Pro Tyr Lys Ala Leu Arg
            115                 120                 125
Asp Leu Lys Glu Ala Arg Gly Leu Leu Ala Lys Asp Leu Ser Val Leu
130                 135                 140
Ala Leu Arg Glu Gly Leu Gly Leu Pro Pro Gly Asp Asp Pro Met Leu
145                 150                 155                 160
Leu Ala Tyr Leu Leu Asp Pro Ser Asn Thr Thr Pro Glu Gly Val Ala
                165                 170                 175
Arg Arg Tyr Gly Gly Glu Trp Thr Glu Glu Ala Gly Glu Arg Ala Ala
                180                 185                 190
Leu Ser Glu Arg Leu Phe Ala Asn Leu Trp Gly Arg Leu Glu Gly Glu
                195                 200                 205
Glu Arg Leu Leu Trp Leu Tyr Arg Glu Val Glu Arg Pro Leu Ser Ala
                210                 215                 220
Val Leu Ala His Met Glu Ala Thr Gly Val Arg Leu Asp Val Ala Tyr
225                 230                 235                 240
Leu Arg Ala Leu Ser Leu Glu Val Ala Glu Glu Ile Ala Arg Leu Glu
                245                 250                 255
Ala Glu Val Phe Arg Leu Ala Gly His Pro Phe Asn Leu Asn Ser Arg
                260                 265                 270
Asp Gln Leu Glu Arg Val Leu Phe Asp Glu Leu Gly Leu Pro Ala Ile
                275                 280                 285
Gly Lys Thr Glu Lys Thr Gly Lys Arg Ser Thr Ser Ala Ala Val Leu
                290                 295                 300
Glu Ala Leu Arg Glu Ala His Pro Ile Val Glu Lys Ile Leu Gln Tyr
305                 310                 315                 320
Arg Glu Leu Thr Lys Leu Lys Ser Thr Tyr Ile Asp Pro Leu Pro Asp
                325                 330                 335
Leu Ile His Pro Arg Thr Gly Arg Leu His Thr Arg Phe Asn Gln Thr
                340                 345                 350
Ala Thr Ala Thr Gly Arg Leu Ser Ser Ser Asp Pro Asn Leu Gln Asn
                355                 360                 365
Ile Pro Val Arg Thr Pro Leu Gly Gln Arg Ile Arg Arg Ala Phe Ile
370                 375                 380
Ala Glu Glu Gly Trp Leu Leu Val Ala Leu Asp Tyr Ser Gln Ile Glu
385                 390                 395                 400
Leu Arg Val Leu Ala His Leu Ser Gly Asp Glu Asn Leu Ile Arg Val
                405                 410                 415
Phe Gln Glu Gly Arg Asp Ile His Thr Glu Thr Ala Ser Trp Met Phe
                420                 425                 430
Gly Val Pro Arg Glu Ala Val Asp Pro Leu Met Arg Arg Ala Ala Lys
                435                 440                 445
Thr Ile Asn Phe Gly Val Leu Tyr Gly Met Ser Ala His Arg Leu Ser
450                 455                 460
Gln Glu Leu Ala Ile Pro Tyr Glu Glu Ala Gln Ala Phe Ile Glu Arg
465                 470                 475                 480
Tyr Phe Gln Ser Phe Pro Lys Val Arg Ala Trp Ile Glu Lys Thr Leu
                485                 490                 495
Glu Glu Gly Arg Arg Arg Gly Tyr Val Glu Thr Leu Phe Gly Arg Arg
                500                 505                 510
Arg Tyr Val Pro Asp Leu Glu Ala Arg Val Lys Ser Val Arg Glu Ala
                515                 520                 525
```

```
Ala Glu Arg Met Ala Phe Asn Met Pro Val Gln Gly Thr Ala Ala Asp
        530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
            565                 570                 575

Pro Lys Glu Arg Ala Glu Ala Val Ala Arg Leu Ala Lys Glu Val Met
        580                 585                 590

Glu Gly Val Tyr Pro Leu Ala Val Pro Leu Glu Val Glu Val Gly Ile
    595                 600                 605

Gly Glu Asp Trp Leu Ser Ala Lys Glu Gly Ile Asp Gly Arg Gly Gly
        610                 615                 620

Gly Gly His His His His His His
625                 630

<210> SEQ ID NO 5
<211> LENGTH: 2763
<212> TYPE: DNA
<213> ORGANISM: Artificial Sequence
<220> FEATURE:
<223> OTHER INFORMATION: Description of Artificial Sequence:Sso7d fused
      to N terminus of full length Taq DNA polymerase,
      Sso7d/full-length Taq fusion protein
<220> FEATURE:
<221> NAME/KEY: CDS
<222> LOCATION: (1)..(2763)
<223> OTHER INFORMATION: Sso7d-Taq fusion protein

<400> SEQUENCE: 5
atgattacga attcgagcgc aaccgtaaag ttcaagtaca aaggcgaaga aaaagaggta      60
gacatctcca agatcaagaa agtatggcgt gtgggcaaga tgatctcctt cacctacgac     120
gagggcggtg gcaagaccgg ccgtggtgcg gtaagcgaaa aggacgcgcc gaaggagctg     180
ctgcagatgc tggagaagca gaaaaagggc ggcgtgtca ctagtgggat gctgccccctc    240 tttgagccca agggccgggt cctcctggtg gacggccacc acctggccta ccgcaccttc     300
cacgccctga agggcctcac caccagccgg ggggagccgg tgcaggcggt ctacggcttc     360
gccaagagcc tcctcaaggc cctcaaggag gacgggggacg cggtgatcgt ggtctttgac     420
gccaaggccc cctccttccg ccacgaggcc tacggggggt acaaggcggg ccgggccccc     480
acgccagagg acttccccg caactcgcc ctcatcaagg agctggtgga cctcctgggg      540
ctggcgcgcc tcgaggtccc gggctacgag cggacgacg tcctggccag cctggccaag     600
aaggcggaaa aggagggcta cgaggtccgc atcctcaccg ccgacaaaga cctttaccag     660
ctcctttccg accgcatcca cgtcctccac cccgaggggt acctcatcac cccggcctgg     720
ctttgggaaa agtacggcct gaggcccgac cagtgggccg actaccgggc cctgaccggg     780
gacgagtccg acaaccttcc cggggtcaag ggcatcgggg agaagacggc gaggaagctt     840
ctggaggagt gggggagcct ggaagccctc tcaagaaacc tggaccggct gaagcccgcc     900
atccgggaga gatcctggc ccacatggac gatctgaagc tctcctggga cctggccaag      960
gtgcgcaccg acctgccct ggaggtggac ttcgccaaaa ggcggagcc cgaccgggag     1020 aggcttaggg cctttctgga gaggcttgag tttggcagcc tcctccacga gttcggcctt     1080
ctggaaagcc ccaaggccct ggaggaggcc cctggccccc gccggaagg ggccttcgtg    1140 ggctttgtgc tttcccgcaa ggagcccatg tgggccgatc ttctggccct ggccgccgcc     1200
agggggggcc gggtccaccg ggccccccgag ccttataaag ccctcaggga cctgaaggag     1260
```

-continued

```
gcgcggggc ttctcgccaa agacctgagc gttctggccc tgaggaaagg ccttggcctc    1320
ccgcccggcg acgaccccat gctcctcgcc tacctcctgg acccttccaa caccaccccc    1380
gaggggtgg cccggcgcta cggcggggag tggacggagg aggcggggga gcgggccgcc    1440
ctttccgaga ggctcttcgc caacctgtgg gggaggcttg aggggagga gaggctcctt    1500
tggctttacc gggaggtgga gaggcccctt tccgctgtcc tggcccacat ggaggccacg    1560
ggggtgcgcc tggacgtggc ctatctcagg gccttgtccc tggaggtggc cgaggagatc    1620
gcccgcctcg aggccgaggt cttccgcctg gccggccacc ccttcaacct caactcccgg    1680
gaccagctgg aaagggtcct ctttgacgag ctagggcttc cgccatcgg caagacggag    1740
aagaccggca gcgctccac cagcgccgcc gtcctggagg ccctccgcga ggcccacccc    1800
atcgtggaga agatcctgca gtaccggag ctcaccaagc tgaagagcac ctacattgac    1860
cccttgccgg acctcatcca ccccaggacg ggccgcctcc acccgcgctt caaccagacg    1920
gccacggcca cggcaggct aagtagctcc gatcccaacc tccagaacat ccccgtccgc    1980
accccgcttg gcagaggat ccgccgggcc ttcatcgccg aggaggggtg gctattggtg    2040
gccctggact atagccagat agagctcagg gtgctggccc acctctccgg cgacgagaac    2100
ctgatccggg tcttccagga ggggcgggac atccacacgg agaccgccag ctggatgttc    2160
ggcgtccccc gggaggccgt ggaccccctg atgcgccggg cggccaagac catcaacttc    2220
ggggtcctct acggcatgtc ggcccaccgc ctctcccagg agctagccat cccttacgag    2280
gaggcccagg ccttcattga gcgctacttt cagagcttcc ccaaggtgcg ggcctggatt    2340
gagaagaccc tggaggaggg caggaggcgg gggtacgtgg agaccctctt cggccgccgc    2400
cgctacgtgc cagacctaga ggcccgggtg aagagcgtgc gggaggcggc cgagcgcatg    2460
gccttcaaca tgcccgtcca gggcaccgcc gccgacctca tgaagctggc tatggtgaag    2520
ctcttcccca ggctggagga aatggggcc aggatgctcc ttcaggtcca cgacgagctg    2580
gtcctcgagg ccccaaaaga gagggcggag gccgtggccc ggctggccaa ggaggtcatg    2640
gagggggtgt atcccctggc cgtgcccctg gaggtggagg tggggatagg ggaggactgg    2700
ctctccgcca aggagggcat tgatggccgc ggcggaggcg gcatcatca tcatcatcat    2760
taa                                                                 2763
```

<210> SEQ ID NO 6
<211> LENGTH: 920
<212> TYPE: PRT
<213> ORGANISM: Artificial Sequence
<220> FEATURE:
<223> OTHER INFORMATION: Description of Artificial Sequence:Sso7d fused
      to N terminus of full length Taq DNA polymerase,
      Sso7d/full-length Taq fusion protein
<220> FEATURE:
<223> OTHER INFORMATION: Sso7d-Taq fusion protein

<400> SEQUENCE: 6

Met Ile Thr Asn Ser Ser Ala Thr Val Lys Phe Lys Tyr Lys Gly Glu
1               5                   10                  15

Glu Lys Glu Val Asp Ile Ser Lys Ile Lys Lys Val Trp Arg Val Gly
            20                  25                  30

Lys Met Ile Ser Phe Thr Tyr Asp Glu Gly Gly Gly Lys Thr Gly Arg
        35                  40                  45

Gly Ala Val Ser Glu Lys Asp Ala Pro Lys Glu Leu Leu Gln Met Leu
    50                  55                  60

-continued

Glu Lys Gln Lys Lys Gly Gly Val Thr Ser Gly Met Leu Pro Leu
65                  70                  75                  80

Phe Glu Pro Lys Gly Arg Val Leu Leu Val Asp Gly His His Leu Ala
            85                  90                  95

Tyr Arg Thr Phe His Ala Leu Lys Gly Leu Thr Thr Ser Arg Gly Glu
            100                 105                 110

Pro Val Gln Ala Val Tyr Gly Phe Ala Lys Ser Leu Leu Lys Ala Leu
            115                 120                 125

Lys Glu Asp Gly Asp Ala Val Ile Val Val Phe Asp Ala Lys Ala Pro
        130                 135                 140

Ser Phe Arg His Glu Ala Tyr Gly Gly Tyr Lys Ala Gly Arg Ala Pro
145                 150                 155                 160

Thr Pro Glu Asp Phe Pro Arg Gln Leu Ala Leu Ile Lys Glu Leu Val
                165                 170                 175

Asp Leu Leu Gly Leu Ala Arg Leu Glu Val Pro Gly Tyr Glu Ala Asp
            180                 185                 190

Asp Val Leu Ala Ser Leu Ala Lys Lys Ala Glu Lys Glu Gly Tyr Glu
            195                 200                 205

Val Arg Ile Leu Thr Ala Asp Lys Asp Leu Tyr Gln Leu Leu Ser Asp
        210                 215                 220

Arg Ile His Val Leu His Pro Glu Gly Tyr Leu Ile Thr Pro Ala Trp
225                 230                 235                 240

Leu Trp Glu Lys Tyr Gly Leu Arg Pro Asp Gln Trp Ala Asp Tyr Arg
                245                 250                 255

Ala Leu Thr Gly Asp Glu Ser Asp Asn Leu Pro Gly Val Lys Gly Ile
            260                 265                 270

Gly Glu Lys Thr Ala Arg Lys Leu Leu Glu Glu Trp Gly Ser Leu Glu
        275                 280                 285

Ala Leu Leu Lys Asn Leu Asp Arg Leu Lys Pro Ala Ile Arg Glu Lys
        290                 295                 300

Ile Leu Ala His Met Asp Asp Leu Lys Leu Ser Trp Asp Leu Ala Lys
305                 310                 315                 320

Val Arg Thr Asp Leu Pro Leu Glu Val Asp Phe Ala Lys Arg Arg Glu
                325                 330                 335

Pro Asp Arg Glu Arg Leu Arg Ala Phe Leu Glu Arg Leu Glu Phe Gly
            340                 345                 350

Ser Leu Leu His Glu Phe Gly Leu Leu Glu Ser Pro Lys Ala Leu Glu
            355                 360                 365

Glu Ala Pro Trp Pro Pro Pro Glu Gly Ala Phe Val Gly Phe Val Leu
        370                 375                 380

Ser Arg Lys Glu Pro Met Trp Ala Asp Leu Leu Ala Leu Ala Ala Ala
385                 390                 395                 400

Arg Gly Gly Arg Val His Arg Ala Pro Glu Pro Tyr Lys Ala Leu Arg
                405                 410                 415

Asp Leu Lys Glu Ala Arg Gly Leu Leu Ala Lys Asp Leu Ser Val Leu
            420                 425                 430

Ala Leu Arg Glu Gly Leu Gly Leu Pro Pro Gly Asp Asp Pro Met Leu
            435                 440                 445

Leu Ala Tyr Leu Leu Asp Pro Ser Asn Thr Thr Pro Glu Gly Val Ala
            450                 455                 460

Arg Arg Tyr Gly Gly Glu Trp Thr Glu Glu Ala Gly Glu Arg Ala Ala
465                 470                 475                 480

Leu Ser Glu Arg Leu Phe Ala Asn Leu Trp Gly Arg Leu Glu Gly Glu

-continued

```
                485                 490                 495
Glu Arg Leu Leu Trp Leu Tyr Arg Glu Val Glu Arg Pro Leu Ser Ala
                500                 505                 510
Val Leu Ala His Met Glu Ala Thr Gly Val Arg Leu Asp Val Ala Tyr
                515                 520                 525
Leu Arg Ala Leu Ser Leu Glu Val Ala Glu Ile Ala Arg Leu Glu
        530                 535                 540
Ala Glu Val Phe Arg Leu Ala Gly His Pro Phe Asn Leu Asn Ser Arg
545                 550                 555                 560
Asp Gln Leu Glu Arg Val Leu Phe Asp Glu Leu Gly Leu Pro Ala Ile
                565                 570                 575
Gly Lys Thr Glu Lys Thr Gly Lys Arg Ser Thr Ser Ala Ala Val Leu
                580                 585                 590
Glu Ala Leu Arg Glu Ala His Pro Ile Val Glu Lys Ile Leu Gln Tyr
                595                 600                 605
Arg Glu Leu Thr Lys Leu Lys Ser Thr Tyr Ile Asp Pro Leu Pro Asp
        610                 615                 620
Leu Ile His Pro Arg Thr Gly Arg Leu His Thr Arg Phe Asn Gln Thr
625                 630                 635                 640
Ala Thr Ala Thr Gly Arg Leu Ser Ser Ser Asp Pro Asn Leu Gln Asn
                645                 650                 655
Ile Pro Val Arg Thr Pro Leu Gly Gln Arg Ile Arg Arg Ala Phe Ile
                660                 665                 670
Ala Glu Glu Gly Trp Leu Leu Val Ala Leu Asp Tyr Ser Gln Ile Glu
        675                 680                 685
Leu Arg Val Leu Ala His Leu Ser Gly Asp Glu Asn Leu Ile Arg Val
        690                 695                 700
Phe Gln Glu Gly Arg Asp Ile His Thr Glu Thr Ala Ser Trp Met Phe
705                 710                 715                 720
Gly Val Pro Arg Glu Ala Val Asp Pro Leu Met Arg Arg Ala Ala Lys
                725                 730                 735
Thr Ile Asn Phe Gly Val Leu Tyr Gly Met Ser Ala His Arg Leu Ser
                740                 745                 750
Gln Glu Leu Ala Ile Pro Tyr Glu Glu Ala Gln Ala Phe Ile Glu Arg
        755                 760                 765
Tyr Phe Gln Ser Phe Pro Lys Val Arg Ala Trp Ile Glu Lys Thr Leu
        770                 775                 780
Glu Glu Gly Arg Arg Gly Tyr Val Glu Thr Leu Phe Gly Arg Arg
785                 790                 795                 800
Arg Tyr Val Pro Asp Leu Glu Ala Arg Val Lys Ser Val Arg Glu Ala
                805                 810                 815
Ala Glu Arg Met Ala Phe Asn Met Pro Val Gln Gly Thr Ala Ala Asp
                820                 825                 830
Leu Met Lys Leu Ala Met Val Lys Leu Phe Pro Arg Leu Glu Glu Met
        835                 840                 845
Gly Ala Arg Met Leu Leu Gln Val His Asp Glu Leu Val Leu Glu Ala
        850                 855                 860
Pro Lys Glu Arg Ala Glu Ala Val Ala Arg Leu Ala Lys Glu Val Met
865                 870                 875                 880
Glu Gly Val Tyr Pro Leu Ala Val Pro Leu Glu Val Glu Val Gly Ile
                885                 890                 895
Gly Glu Asp Trp Leu Ser Ala Lys Glu Gly Ile Asp Gly Arg Gly Gly
                900                 905                 910
```

Gly Gly His His His His His His
        915                 920

<210> SEQ ID NO 7
<211> LENGTH: 2535
<212> TYPE: DNA
<213> ORGANISM: Artificial Sequence
<220> FEATURE:
<223> OTHER INFORMATION: Description of Artificial Sequence:Sso7d fused
      to C terminus of Pyrococcus furiosus DNA polymerase
      polI (Pfu), Pfu-Sso7d fusion protein
<220> FEATURE:
<221> NAME/KEY: CDS
<222> LOCATION: (1)..(2535)
<223> OTHER INFORMATION: Pfu-Sso7d fusion protein

<400> SEQUENCE: 7

| | | | | | |
|---|---|---|---|---|---|
| atgattttag | atgtggatta | cataactgaa | gaaggaaaac | ctgttattag | gctattcaaa | 60 |
| aaagagaacg | aaaatttaa | gatagagcat | gatagaactt | ttagaccata | catttacgct | 120 |
| cttctcaggg | atgattcaaa | gattgaagaa | gttaagaaaa | taacggggga | aaggcatgga | 180 |
| aagattgtga | aattgttga | tgtagagaag | gttgagaaaa | agtttctcgg | caagcctatt | 240 |
| accgtgtgga | aactttattt | ggaacatccc | caagatgttc | ccactattag | agaaaaagtt | 300 |
| agagaacatc | cagcagttgt | ggacatcttc | gaatacgata | ttccatttgc | aaagagatac | 360 |
| ctcatcgaca | aggcctaat | accaatggag | ggggaagaag | agctaaagat | tcttgccttc | 420 |
| gatatagaaa | ccctctatca | cgaaggagaa | gagtttggaa | aaggcccaat | tataatgatt | 480 |
| agttatgcag | atgaaaatga | agcaaggtg | attacttgga | aaaacataga | tcttccatac | 540 |
| gttgaggttg | tatcaagcga | gagagagatg | ataaagagat | tctcaggat | atcagggag | 600 |
| aaggatcctg | acattatagt | tacttataat | ggagactcat | cgacttccc | atatttagcg | 660 |
| aaaaggcag | aaaaacttgg | gattaaatta | accattggaa | gagatggaag | cgagcccaag | 720 |
| atgcagagaa | taggcgatat | gacggctgta | gaagtcaagg | gaagaataca | tttcgacttg | 780 |
| tatcatgtaa | taacaaggac | aataaatctc | ccaacataca | cactagaggc | tgtatatgaa | 840 |
| gcaattttg | aaagccaaa | ggagaaggta | tacgccgacg | atagcaaa | agcctgggaa | 900 |
| agtggagaga | accttgagag | agttgccaaa | tactcgatgg | aagatgcaaa | ggcaacttat | 960 |
| gaactcggga | agaattcct | tccaatggaa | attcagcttt | caagattagt | tggacaacct | 1020 |
| ttatgggatg | tttcaaggtc | aagcacaggg | aaccttgtag | agtggttctt | acttaggaaa | 1080 |
| gcctacgaaa | gaaacgaagt | agctccaaac | aagccaagtg | aagaggagta | tcaaagaagg | 1140 |
| ctcagggaga | gctacacagg | tggattcgtt | aaagagccag | aaaggggtt | gtgggaaaac | 1200 |
| atagtatacc | tagattttag | agccctatat | ccctcgatta | taattaccca | caatgttct | 1260 |
| cccgatactc | taaatcttga | gggatgcaag | aactatgata | tcgctcctca | agtaggccac | 1320 |
| aagttctgca | aggacatccc | tggttttata | ccaagtctct | tgggacattt | gttagaggaa | 1380 |
| agacaaaaga | ttaagacaaa | aatgaaggaa | actcaagatc | ctatagaaaa | aatactcctt | 1440 |
| gactatagac | aaaaagcgat | aaaactctta | gcaaattctt | tctacggata | ttatggctat | 1500 |
| gcaaaagcaa | gatggtactg | taaggagtgt | gctgagagcg | ttactgcctg | gggaagaaag | 1560 |
| tacatcgagt | tagtatggaa | ggagctcgaa | gaaaagtttg | gatttaaagt | cctctacatt | 1620 |
| gacactgatg | gtctctatgc | aactatccca | ggaggagaaa | gtgaggaaat | aaagaaaaag | 1680 |
| gctctagaat | ttgtaaaata | cataaattca | agctccctg | gactgctaga | gcttgaatat | 1740 |
| gaagggtttt | ataagagggg | attcttcgtt | acgaagaaga | ggtatgcagt | aatagatgaa | 1800 |

```
gaaggaaaag tcattactcg tggtttagag atagttagga gagattggag tgaaattgca    1860
aaagaaactc aagctagagt tttggagaca atactaaaac acggagatgt tgaagaagct    1920
gtgagaatag taaagaagt aatacaaaag cttgccaatt atgaaattcc accagagaag    1980
ctcgcaatat atgagcagat aacaagacca ttacatgagt ataaggcgat aggtcctcac    2040
gtagctgttg caaagaaact agctgctaaa ggagttaaaa taaagccagg aatggtaatt    2100
ggatacatag tacttagagg cgatggtcca attagcaata gggcaattct agctgaggaa    2160
tacgatccca aaaagcacaa gtatgacgca gaatattaca ttgagaacca ggttcttcca    2220
gcggtactta ggatattgga gggatttgga tacagaaagg aagacctcag ataccaaaag    2280
acaagacaag tcggcctaac ttcctggctt aacattaaaa aatccggtac cggcggtggc    2340
ggtgcaaccg taaagttcaa gtacaaaggc gaagaaaaag aggtagacat ctccaagatc    2400
aagaaagtat ggcgtgtggg caagatgatc tccttcacct acgacgaggg cggtggcaag    2460
accggccgtg gtgcggtaag cgaaaaggac gcgccgaagg agctgctgca gatgctggag    2520
aagcagaaaa agtga                                                     2535

<210> SEQ ID NO 8
<211> LENGTH: 844
<212> TYPE: PRT
<213> ORGANISM: Artificial Sequence
<220> FEATURE:
<223> OTHER INFORMATION: Description of Artificial Sequence:Sso7d fused
      to C terminus of Pyrococcus furiosus DNA polymerase
      polI (Pfu), Pfu-Sso7d fusion protein
<220> FEATURE:
<223> OTHER INFORMATION: Pfu-Sso7d fusion protein

<400> SEQUENCE: 8

Met Ile Leu Asp Val Asp Tyr Ile Thr Glu Glu Gly Lys Pro Val Ile
 1               5                  10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205
```

-continued

Tyr Asn Gly Asp Ser Phe Asp Phe Pro Tyr Leu Ala Lys Arg Ala Glu
         210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                     245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
             275                 280                 285

Lys Val Tyr Ala Asp Glu Ile Ala Lys Ala Trp Glu Ser Gly Glu Asn
290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                 325                 330                 335

Val Gly Gln Pro Leu Trp Asp Val Ser Arg Ser Ser Thr Gly Asn Leu
             340                 345                 350

Val Glu Trp Phe Leu Leu Arg Lys Ala Tyr Glu Arg Asn Glu Val Ala
         355                 360                 365

Pro Asn Lys Pro Ser Glu Glu Glu Tyr Gln Arg Arg Leu Arg Glu Ser
     370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                 405                 410                 415

His Asn Val Ser Pro Asp Thr Leu Asn Leu Glu Gly Cys Lys Asn Tyr
             420                 425                 430

Asp Ile Ala Pro Gln Val Gly His Lys Phe Cys Lys Asp Ile Pro Gly
         435                 440                 445

Phe Ile Pro Ser Leu Leu Gly His Leu Leu Glu Glu Arg Gln Lys Ile
     450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                 485                 490                 495

Tyr Tyr Gly Tyr Ala Lys Ala Arg Trp Tyr Cys Lys Glu Cys Ala Glu
             500                 505                 510

Ser Val Thr Ala Trp Gly Arg Lys Tyr Ile Glu Leu Val Trp Lys Glu
         515                 520                 525

Leu Glu Glu Lys Phe Gly Phe Lys Val Leu Tyr Ile Asp Thr Asp Gly
     530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                 565                 570                 575

Glu Leu Glu Tyr Glu Gly Phe Tyr Lys Arg Gly Phe Phe Val Thr Lys
             580                 585                 590

Lys Arg Tyr Ala Val Ile Asp Glu Glu Gly Lys Val Ile Thr Arg Gly
         595                 600                 605

Leu Glu Ile Val Arg Arg Asp Trp Ser Glu Ile Ala Lys Glu Thr Gln
     610                 615                 620

```
Ala Arg Val Leu Glu Thr Ile Leu Lys His Gly Asp Val Glu Ala
625                 630                 635                 640

Val Arg Ile Val Lys Glu Val Ile Gln Lys Leu Ala Asn Tyr Glu Ile
            645                 650                 655

Pro Pro Glu Lys Leu Ala Ile Tyr Glu Gln Ile Thr Arg Pro Leu His
                660                 665                 670

Glu Tyr Lys Ala Ile Gly Pro His Val Ala Val Ala Lys Lys Leu Ala
            675                 680                 685

Ala Lys Gly Val Lys Ile Lys Pro Gly Met Val Ile Gly Tyr Ile Val
690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
            755                 760                 765

Trp Leu Asn Ile Lys Lys Ser Gly Thr Gly Gly Gly Ala Thr Val
770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
            835                 840

<210> SEQ ID NO 9
<211> LENGTH: 1904
<212> TYPE: DNA
<213> ORGANISM: Artificial Sequence
<220> FEATURE:
<223> OTHER INFORMATION: Description of Artificial Sequence:Sulfolobus
      acidocaldarius Sac7d fused to the N terminus of
      deltaTaq, Sac7d-deltaTaq fusion protein
<220> FEATURE:
<221> NAME/KEY: CDS
<222> LOCATION: (1)..(1904)
<223> OTHER INFORMATION: Sac7d-deltaTaq fusion protein

<400> SEQUENCE: 9
atgattacga attcgacggt gaaggtaaag ttcaagtata agggtgaaga gaaagaagta      60
gacacttcaa agataaagaa ggtttggaga gtaggcaaaa tggtgtcctt tacctatgac    120
gacaatggta agacaggtag aggagctgta agcgagaaag atgctccaaa agaattatta    180
gacatgttag caagagcaga agagagaag aaaggcggcg gtgtcactag tcccaaggcc    240
ctggaggagg cccctggcc cccgccggaa ggggccttcg tgggctttgt gctttcccgc    300
aaggagccca tgtgggccga tcttctggcc ctggccgccg ccaggggggg ccgggtccac    360
cgggcccccg agcctataaa agccctcagg gacctgaagg aggcgcgggg gcttctcgcc    420
aaagacctga gcgttctggc cctgagggaa ggccttggcc tcccgcccgg cgacgacccc    480
atgctcctcg cctacctcct ggaccctttcc aacaccaccc ccgaggggt ggcccggcgc    540 tacggcgggga gtggacgga ggaggcgggg agcggccg cccttcgga gaggctcttc    600 gccaacctgt ggggggaggct tgaggggag gagaggctcc tttggcttta ccggagggtg    660
```

```
gagaggcccc tttccgctgt cctggcccac atggaggcca cggggtgcg cctggacgtg    720 gcctatctca gggccttgtc cctggaggtg gccgaggaga tcgcccgcct cgaggccggg    780
tcttccgcct ggccggccac cccttcaacc tcaactcccg ggaccagctg aaagggtcc    840 tctttgacga gctagggctt cccgccatcg gcaagacgga gaagaccggc aagcgctcca    900
ccagcgccgc cgtcctggag gccctccgcg aggcccaccc catcgtggag aagatcctgc    960
agtaccggga gctcaccaag ctgaagagca cctacattga ccccttgccg gacctcatcc   1020
accccaggac gggccgcctc acacccgct tcaaccagac ggccacggcc acgggcaggc   1080
taagtagctc cgatcccaac ctccagaaca tccccgtccg caccccgctt ggcagagga   1140 tccgccgggc cttcatcgcc gaggaggggt ggctattggt ggccctggac tatagccaga   1200
tagagctcag ggtgctggcc cacctctccg cgacgagaa cctgatccgg gtcttccagg   1260
aggggcggga catccacacg gagaccgcca gctggatgtt cggcgtcccc cgggaggccg   1320
tggaccccct gatgcgccgg gcggccaaga ccatcaactt cggggtcctc tacggcatgt   1380
cggcccaccg cctctcccag gagctagcca tcccttacga ggaggcccag gccttcattg   1440
agcgctactt tcagagcttc cccaaggtgc gggcctggat tgagaagacc ctggaggagg   1500
gcaggaggcg ggggtacgtg gagaccctct tcggccgccg ccgctacgtg ccagacctag   1560
aggcccgggt gaagagcgtg cgggaggcgg ccgagcgcat ggccttcaac atgcccgtcc   1620
agggcaccgc cgccgacctc atgaagctgg ctatggtgaa gctcttcccc aggctggagg   1680
aaatgggggc caggatgctc cttcaggtcc acgacgagct ggtcctcgag gccccaaaag   1740
agagggcgga ggccgtggcc cggctggcca aggaggtcat ggagggggtg tatcccctgg   1800
ccgtgcccct ggaggtggag gtggggatag ggaggactg gctctccgcc aaggagggca   1860
ttgatggccg cggcggaggc gggcatcatc atcatcatca ttaa                     1904
```

<210> SEQ ID NO 10
<211> LENGTH: 634
<212> TYPE: PRT
<213> ORGANISM: Artificial Sequence
<220> FEATURE:
<223> OTHER INFORMATION: Description of Artificial Sequence:Sulfolobus
    acidocaldarius Sac7d fused to the N terminus of
    deltaTaq, Sac7d-deltaTaq fusion protein
<220> FEATURE:
<223> OTHER INFORMATION: Sac7d-deltaTaq fusion protein

<400> SEQUENCE: 10

Met Ile Thr Asn Ser Thr Val Lys Val Lys Phe Lys Tyr Lys Gly Glu
 1               5                  10                  15

Glu Lys Glu Val Asp Thr Ser Lys Ile Lys Lys Val Trp Arg Val Gly
            20                  25                  30

Lys Met Val Ser Phe Thr Tyr Asp Asp Asn Gly Lys Thr Gly Arg Gly
        35                  40                  45

Ala Val Ser Glu Lys Asp Ala Pro Lys Glu Leu Leu Asp Met Leu Ala
    50                  55                  60

Arg Ala Glu Arg Glu Lys Lys Gly Gly Val Thr Ser Pro Lys Ala
65                  70                  75                  80

Leu Glu Glu Ala Pro Trp Pro Pro Glu Gly Ala Phe Val Gly Phe
                85                  90                  95

Val Leu Ser Arg Lys Glu Pro Met Trp Ala Asp Leu Leu Ala Leu Ala
            100                 105                 110

Ala Ala Arg Gly Gly Arg Val His Arg Ala Pro Glu Pro Tyr Lys Ala

-continued

```
                115                 120                 125
Leu Arg Asp Leu Lys Glu Ala Arg Gly Leu Leu Ala Lys Asp Leu Ser
130                 135                 140

Val Leu Ala Leu Arg Glu Gly Leu Gly Leu Pro Pro Gly Asp Asp Pro
145                 150                 155                 160

Met Leu Leu Ala Tyr Leu Leu Asp Pro Ser Asn Thr Thr Pro Glu Gly
                165                 170                 175

Val Ala Arg Arg Tyr Gly Gly Glu Trp Thr Glu Glu Ala Gly Glu Arg
                180                 185                 190

Ala Ala Leu Ser Glu Arg Leu Phe Ala Asn Leu Trp Gly Arg Leu Glu
                195                 200                 205

Gly Glu Glu Arg Leu Leu Trp Leu Tyr Arg Glu Val Glu Arg Pro Leu
210                 215                 220

Ser Ala Val Leu Ala His Met Glu Ala Thr Gly Val Arg Leu Asp Val
225                 230                 235                 240

Ala Tyr Leu Arg Ala Leu Ser Leu Glu Val Ala Glu Glu Ile Ala Arg
                245                 250                 255

Leu Glu Ala Glu Val Phe Arg Leu Ala Gly His Pro Phe Asn Leu Asn
                260                 265                 270

Ser Arg Asp Gln Leu Glu Arg Val Leu Phe Asp Glu Leu Gly Leu Pro
                275                 280                 285

Ala Ile Gly Lys Thr Glu Lys Thr Gly Lys Arg Ser Thr Ser Ala Ala
290                 295                 300

Val Leu Glu Ala Leu Arg Glu Ala His Pro Ile Val Glu Lys Ile Leu
305                 310                 315                 320

Gln Tyr Arg Glu Leu Thr Lys Leu Lys Ser Thr Tyr Ile Asp Pro Leu
                325                 330                 335

Pro Asp Leu Ile His Pro Arg Thr Gly Arg Leu His Thr Arg Phe Asn
                340                 345                 350

Gln Thr Ala Thr Ala Thr Gly Arg Leu Ser Ser Ser Asp Pro Asn Leu
                355                 360                 365

Gln Asn Ile Pro Val Arg Thr Pro Leu Gly Gln Arg Ile Arg Arg Ala
370                 375                 380

Phe Ile Ala Glu Glu Gly Trp Leu Leu Val Ala Leu Asp Tyr Ser Gln
385                 390                 395                 400

Ile Glu Leu Arg Val Leu Ala His Leu Ser Gly Asp Glu Asn Leu Ile
                405                 410                 415

Arg Val Phe Gln Glu Gly Arg Asp Ile His Thr Glu Thr Ala Ser Trp
                420                 425                 430

Met Phe Gly Val Pro Arg Glu Ala Val Asp Pro Leu Met Arg Arg Ala
                435                 440                 445

Ala Lys Thr Ile Asn Phe Gly Val Leu Tyr Gly Met Ser Ala His Arg
                450                 455                 460

Leu Ser Gln Glu Leu Ala Ile Pro Tyr Glu Glu Ala Gln Ala Phe Ile
465                 470                 475                 480

Glu Arg Tyr Phe Gln Ser Phe Pro Lys Val Arg Ala Trp Ile Glu Lys
                485                 490                 495

Thr Leu Glu Glu Gly Arg Arg Gly Tyr Val Glu Thr Leu Phe Gly
                500                 505                 510

Arg Arg Arg Tyr Val Pro Asp Leu Glu Ala Arg Val Lys Ser Val Arg
                515                 520                 525

Glu Ala Ala Glu Arg Met Ala Phe Asn Met Pro Val Gln Gly Thr Ala
530                 535                 540
```

-continued

```
Ala Asp Leu Met Lys Leu Ala Met Val Lys Leu Phe Pro Arg Leu Glu
545                 550                 555                 560

Glu Met Gly Ala Arg Met Leu Leu Gln Val His Asp Glu Leu Val Leu
                565                 570                 575

Glu Ala Pro Lys Glu Arg Ala Glu Ala Val Ala Arg Leu Ala Lys Glu
            580                 585                 590

Val Met Glu Gly Val Tyr Pro Leu Ala Val Pro Leu Glu Val Glu Val
        595                 600                 605

Gly Ile Gly Glu Asp Trp Leu Ser Ala Lys Glu Gly Ile Asp Gly Arg
    610                 615                 620

Gly Gly Gly Gly His His His His His His
625                 630
```

<210> SEQ ID NO 11
<211> LENGTH: 1965
<212> TYPE: DNA
<213> ORGANISM: Artificial Sequence
<220> FEATURE:
<223> OTHER INFORMATION: Description of Artificial Sequence:lysine-rich
      peptide fused to N terminus of deltaTaq,
      polylysine (PL)-deltaTaq fusion protein
<220> FEATURE:
<221> NAME/KEY: CDS
<222> LOCATION: (1)..(1965)
<223> OTHER INFORMATION: PL-deltaTaq fusion protien

<400> SEQUENCE: 11

```
atgattacga attcgaagaa aaagaaaaag aaaaagcgta agaaacgcaa aaagaaaaag      60
aaaggcggcg gtgtcactag tggcgcaacc gtaaagttca agtacaaagg cgaagaaaaa     120
gaggtagaca tctccaagat caagaaagta tggcgtgtgg gcaagatgat ctccttcacc     180
tacgacgagg gcggtggcaa gaccggccgt ggtgcggtaa gcgaaaagga cgcgccgaag     240
gagctgctgc agatgctgga gaagcagaaa aagggcggcg tgtcaccagt cccaaggcc      300 ctggaggagg ccccctggcc cccgccggaa ggggccttcg tgggctttgt gctttcccgc     360
aaggagccca tgtgggccga tcttctggcc ctggccgccg ccaggggggg ccgggtccac     420 cgggccccg agcctataaa gcccctcagg acctgaagg aggcgcgggg gcttctcgcc       480
aaagacctga gcgttctggc cctgagggaa ggccttggcc tcccgcccgg cgacgacccc     540
atgctcctcg cctacctcct ggaccttcc aacaccaccc cgagggggt ggcccggcgc       600 tacggcgggg agtggacgga ggaggcgggg gagcgggccg ccctttccga gaggctcttc     660
gccaacctgt gggggaggct tgaggggag gagaggctcc tttggctta ccggaggtg       720 gagaggcccc tttccgctgt cctggcccac atggaggcca ggggggtgcg cctggacgtg     780
gcctatctca gggccttgtc cctggaggtg gccgaggaga tcgcccgcct cgaggccgag     840
gtcttccgcc tggccggcca cccccttcaac ctcaactccc gggaccagct ggaaagggtc     900
ctctttgacg agctagggct tcccgccatc ggcaagacgg agaagacggg caagcgctcc     960
accagcgccg ccgtcctgga ggcctccgc gaggccacc ccatcgtgga aagatcctg       1020 cagtaccggg agctcaccaa gctgaagagc acctacattg acccctgcc ggacctcatc    1080 caccccagga cggccgcct ccacaccgc ttcaaccaga cggccacggc cacgggcagg      1140
ctaagtagct ccgatcccaa cctccagaac atcccgtcc gcaccccgct gggcagagg       1200 atccgccggg ccttcatcgc cgaggagggg tggctattgg tggccctgga ctatagccag     1260
atagagctca gggtgctggc ccacctctcc ggcgacgaga acctgatccg ggtcttccag     1320
```

-continued

```
gaggggcggg acatccacac ggagaccgcc agctggatgt cggcgtcccc ccggaggcc        1380
gtggacccc tgatgcgccg gcggccaag accatcaact cggggtcct ctacggcatg         1440
tcggcccacc gcctctccca ggagctagcc atcccttacg aggaggccca ggccttcatt      1500
gagcgctact ttcagagctt cccaaggtg cgggcctgga ttgagaagac cctggaggag       1560
ggcaggaggc gggggtacgt ggagaccctc ttcggccgcc gccgctacgt gccagaccta      1620
gaggcccggg tgaagagcgt gcgggaggcg gccgagcgca tggccttcaa catgcccgtc      1680
cagggcaccg ccgccgacct catgaagctg gctatggtga agctcttccc caggctggag     1740
gaaatggggg ccaggatgct ccttcaggtc cacgacgagc tggtcctcga ggcccccaaaa    1800
gagagggcgg aggccgtggc ccggctggcc aaggaggtca tggagggggt gtatcccctg     1860
gccgtgcccc tggaggtgga ggtggggata ggggaggact ggctctccgc caaggagggc     1920
attgatggcc gcggcggagg cgggcatcat catcatcatc attaa                      1965
```

<210> SEQ ID NO 12
<211> LENGTH: 654
<212> TYPE: PRT
<213> ORGANISM: Artificial Sequence
<220> FEATURE:
<223> OTHER INFORMATION: Description of Artificial Sequence:lysine-rich
      peptide fused to N terminus of deltaTaq,
      polylysine (PL)-deltaTaq fusion protein
<220> FEATURE:
<223> OTHER INFORMATION: PL-deltaTaq fusion protein

<400> SEQUENCE: 12

```
Met Ile Thr Asn Ser Lys Lys Lys Lys Lys Lys Arg Lys Lys Arg
 1               5                  10                  15

Lys Lys Lys Lys Lys Gly Gly Gly Val Thr Ser Gly Ala Thr Val Lys
                20                  25                  30

Phe Lys Tyr Lys Gly Glu Glu Lys Glu Val Asp Ile Ser Lys Ile Lys
            35                  40                  45

Lys Val Trp Arg Val Gly Lys Met Ile Ser Phe Thr Tyr Asp Glu Gly
        50                  55                  60

Gly Gly Lys Thr Gly Arg Gly Ala Val Ser Glu Lys Asp Ala Pro Lys
    65                  70                  75                  80

Glu Leu Leu Gln Met Leu Glu Lys Gln Lys Lys Gly Gly Gly Val Thr
                85                  90                  95

Ser Pro Lys Ala Leu Glu Glu Ala Pro Trp Pro Pro Glu Gly Ala
                100                 105                 110

Phe Val Gly Phe Val Leu Ser Arg Lys Glu Pro Met Trp Ala Asp Leu
            115                 120                 125

Leu Ala Leu Ala Ala Ala Arg Gly Gly Arg Val His Arg Ala Pro Glu
        130                 135                 140

Pro Tyr Lys Ala Leu Arg Asp Leu Lys Glu Ala Arg Gly Leu Leu Ala
145                 150                 155                 160

Lys Asp Leu Ser Val Leu Ala Leu Arg Glu Gly Leu Gly Leu Pro Pro
                165                 170                 175

Gly Asp Asp Pro Met Leu Leu Ala Tyr Leu Leu Asp Pro Ser Asn Thr
            180                 185                 190

Thr Pro Glu Gly Val Ala Arg Arg Tyr Gly Gly Glu Trp Thr Glu Glu
        195                 200                 205

Ala Gly Glu Arg Ala Ala Leu Ser Glu Arg Leu Phe Ala Asn Leu Trp
    210                 215                 220

Gly Arg Leu Glu Gly Glu Glu Arg Leu Leu Trp Leu Tyr Arg Glu Val
```

```
            225                 230                 235                 240
Glu Arg Pro Leu Ser Ala Val Leu Ala His Met Glu Ala Thr Gly Val
                245                 250                 255

Arg Leu Asp Val Ala Tyr Leu Arg Ala Leu Ser Leu Glu Val Ala Glu
                260                 265                 270

Glu Ile Ala Arg Leu Glu Ala Glu Val Phe Arg Leu Ala Gly His Pro
                275                 280                 285

Phe Asn Leu Asn Ser Arg Asp Gln Leu Glu Arg Val Leu Phe Asp Glu
                290                 295                 300

Leu Gly Leu Pro Ala Ile Gly Lys Thr Glu Lys Thr Gly Lys Arg Ser
305                 310                 315                 320

Thr Ser Ala Ala Val Leu Glu Ala Leu Arg Glu Ala His Pro Ile Val
                325                 330                 335

Glu Lys Ile Leu Gln Tyr Arg Glu Leu Thr Lys Leu Lys Ser Thr Tyr
                340                 345                 350

Ile Asp Pro Leu Pro Asp Leu Ile His Pro Arg Thr Gly Arg Leu His
                355                 360                 365

Thr Arg Phe Asn Gln Thr Ala Thr Ala Thr Gly Arg Leu Ser Ser Ser
370                 375                 380

Asp Pro Asn Leu Gln Asn Ile Pro Val Arg Thr Pro Leu Gly Gln Arg
385                 390                 395                 400

Ile Arg Arg Ala Phe Ile Ala Glu Glu Gly Trp Leu Leu Val Ala Leu
                405                 410                 415

Asp Tyr Ser Gln Ile Glu Leu Arg Val Leu Ala His Leu Ser Gly Asp
                420                 425                 430

Glu Asn Leu Ile Arg Val Phe Gln Glu Gly Arg Asp Ile His Thr Glu
                435                 440                 445

Thr Ala Ser Trp Met Phe Gly Val Pro Arg Glu Ala Val Asp Pro Leu
                450                 455                 460

Met Arg Arg Ala Ala Lys Thr Ile Asn Phe Gly Val Leu Tyr Gly Met
465                 470                 475                 480

Ser Ala His Arg Leu Ser Gln Glu Leu Ala Ile Pro Tyr Glu Glu Ala
                485                 490                 495

Gln Ala Phe Ile Glu Arg Tyr Phe Gln Ser Phe Pro Lys Val Arg Ala
                500                 505                 510

Trp Ile Glu Lys Thr Leu Glu Glu Gly Arg Arg Arg Gly Tyr Val Glu
                515                 520                 525

Thr Leu Phe Gly Arg Arg Arg Tyr Val Pro Asp Leu Glu Ala Arg Val
                530                 535                 540

Lys Ser Val Arg Glu Ala Ala Glu Arg Met Ala Phe Asn Met Pro Val
545                 550                 555                 560

Gln Gly Thr Ala Ala Asp Leu Met Lys Leu Ala Met Val Lys Leu Phe
                565                 570                 575

Pro Arg Leu Glu Glu Met Gly Ala Arg Met Leu Leu Gln Val His Asp
                580                 585                 590

Glu Leu Val Leu Glu Ala Pro Lys Glu Arg Ala Glu Ala Val Ala Arg
                595                 600                 605

Leu Ala Lys Glu Val Met Glu Gly Val Tyr Pro Leu Ala Val Pro Leu
                610                 615                 620

Glu Val Glu Val Gly Ile Gly Glu Asp Trp Leu Ser Ala Lys Glu Gly
625                 630                 635                 640

Ile Asp Gly Arg Gly Gly Gly His His His His His
                645                 650
```

```
<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 13

His His His His His His
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      anti-DYKDDDDK epitope tag

<400> SEQUENCE: 14

Asp Tyr Lys Asp Asp Asp Asp Lys
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:synthetic
      peptide linker

<400> SEQUENCE: 15

Gly Gly Val Thr
 1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:peptide
      linker

<400> SEQUENCE: 16

Gly Thr Gly Gly Gly Gly
 1               5

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence:lysine-rich
      peptide

<400> SEQUENCE: 17

Asn Ser Lys Lys Lys Lys Lys Lys Arg Lys Lys Arg Lys Lys Lys
 1               5                  10                  15

Gly Gly Gly Val Thr
                20
```

NUCLEIC ACID MODIFYING ENZYMES

CROSS-REFERENCES TO RELATED APPLICATIONS

This application is a continuation of U.S. application Ser. No. 13/850,048, filed Mar. 25, 2013, which is a continuation of U.S. application Ser. No. 13/047,638, filed Mar. 14, 2011, which is a continuation of U.S. application Ser. No. 10/256,705, filed Sep. 27, 2002 and issued as U.S. Pat. No. 7,919,296, which is a continuation of U.S. application Ser. No. 09/640,958, filed Aug. 16, 2000 and issued as U.S. Pat. No. 6,627,424, which claims the benefit of U.S. Provisional Application Ser. No. 60/207,567 filed May 26, 2000, the disclosures of which are herein incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-1-5_SEQTXT.TXT, created on Oct. 18, 2013, 50,330 bytes, machine format IBM-PC, MS-Windows operating system, is hereby incorporated by reference.

FIELD OF THE INVENTION

This invention provides for an improved generation of novel nucleic acid modifying enzymes. The improvement is the joining of a sequence-non-specific nucleic-acid-binding domain to the enzyme in a manner that enhances the ability of the enzyme to bind and catalytically modify the nucleic acid.

BACKGROUND OF THE INVENTION

The efficiency of a nucleic acid modifying enzyme, i.e., the amount of modified product generated by the enzyme per binding event, can be enhanced by increasing the stability of the modifying enzyme/nucleic acid complex. The prior art has suggested that attachment of a high probability binding site, e.g., a positively charged binding tail, to a nucleic acid modifying enzyme can increase the frequency with which the modifying enzyme interacts with the nucleic acid (see, e.g., U.S. Pat. No. 5,474,911). The present invention now provides novel modifying enzymes in which the double-stranded conformation of the nucleic acid is stabilized and the efficiency of the enzyme increased by joining a sequence-non-specific double-stranded nucleic acid binding domain to the enzyme, or its catalytic domain. The modifying proteins that are processive in nature exhibit increased processivity when joined to a binding domain compared to the enzyme alone. Moreover, both processive and non-processive modifying enzymes exhibit increased efficiency at higher temperatures when joined to a typical binding domain described herein.

BRIEF SUMMARY OF THE INVENTION

The present invention provides a protein consisting of at least two heterologous domains wherein a first domain that is a sequence-non-specific double-stranded nucleic acid binding domain is joined to a second domain that is a catalytic nucleic acid modifying domain having a processive nature, where the presence of the sequence-non-specific double-stranded nucleic acid binding domain enhances the processive nature of the nucleic acid modifying domain compared to an identical protein not having a sequence-non-specific nucleic acid binding domain joined thereto. In one aspect of the invention, the nucleic acid modifying domain can have a polymerase activity, which can be thermally stable, e.g., a *Thermus* polymerase domain. In alternative embodiments, the catalytic domain is an RNA polymerase, a reverse transcriptase, a methylase, a 3' or 5' exonuclease, a gyrase, or a topoisomerase.

In a particular embodiment, a sequence-non-specific nucleic acid binding domain of the protein can specifically bind to polyclonal antibodies generated against Sac7d or Sso7d. Alternatively, the sequence-non-specific nucleic acid binding domain can contain a 50 amino acid subsequence that has 50% amino acid similarity to Sso7d. The nucleic acid binding domain can also be Sso7d.

In another embodiment, a protein of the invention contains a sequence-non-specific double-stranded nucleic acid binding domain that specifically binds to polyclonal antibodies generated against a PCNA homolog of *Pyrococcus furiosus*, or can be a PCNA homolog of *Pyrococcus furiosus*.

The invention also provides a protein consisting of at least two heterologous domains, wherein a first domain that is a sequence-non-specific double-stranded nucleic acid binding domain is joined to a second domain that is a catalytic nucleic-acid-modifying domain, where the presence of the sequence-non-specific nucleic-acid binding domain stabilizes the double-stranded conformation of a nucleic acid by at least 1° C. compared to an identical protein not having a sequence-non-specific nucleic acid binding domain joined thereto. The nucleic acid modifying domain of such a protein can have polymerase activity, which can be thermally stable. The nucleic-acid-modifying domain can also have RNA polymerase, reverse transcriptase, methylase, 3' or 5' exonuclease, gyrase, or topoisomerase activity.

In further embodiments, the sequence-non-specific nucleic-acid-binding domain can specifically bind to polyclonal antibodies generated against either Sac7d or Sso7d, frequently Sso7d, or contains a 50 amino acid subsequence containing 50% or 75% amino acid similarity to Sso7d. Often, the sequence-non-specific nucleic-acid-binding domain is Sso7d.

Proteins of the invention include a protein wherein the sequence-non-specific nucleic-acid-binding domain specifically binds to polyclonal antibodies generated against the PCNA homolog of *Pyrococcus furiosus*; often the binding domain is the PCNA homolog of *Pyrococcus furiosus*.

In another aspect, the invention provides methods of modifying nucleic acids using the proteins. One embodiment is a method of modifying a nucleic acid in an aqueous solution by: (i) contacting the nucleic acid with a protein comprising at least two heterologous domains, wherein a first domain that is a sequence-non-specific nucleic-acid-binding domain is joined to a second domain that is a catalytic nucleic-acid-modifying domain having a processive nature, where the sequence-non-specific nucleic-acid-binding domain: a. binds to double-stranded nucleic acid, and b. enhances the processivity of the enzyme compared to an identical enzyme not having the sequence non-specific nucleic-acid-binding domain fused to it, and wherein the solution is at a temperature and of a composition that permits the binding domain to bind to the nucleic acid and the enzyme to function in a catalytic manner; and (ii) permitting the catalytic domain to modify the nucleic acid in the solution.

In another aspect, the invention provides a method of modifying a nucleic acid by: (i) contacting the nucleic acid with an aqueous solution containing a protein having at least two heterologous domains, wherein a first domain that is a sequence-non-specific double-stranded nucleic-acid-binding domain is joined to a second domain that is a catalytic nucleic-acid-modifying domain, where the presence of the sequence-non-specific nucleic-acid-binding domain stabilizes the formation of a double-stranded nucleic acid compared to an otherwise identical protein not having the sequence-non-specific nucleic-acid-binding domain joined to it; and, wherein the solution is at a temperature and of a composition that permits the binding domain to bind to the nucleic acid and the enzyme to function in a catalytic manner; and (ii) permitting the catalytic domain to modify the nucleic acid in the solution. The methods of modifying a nucleic acid can employ any of the protein embodiments described herein.

Definitions

"Archaeal small basic DNA-binding protein" refers to protein of between 50-75 amino acids having either 50% homology to a natural Archaeal small basic DNA-binding protein such as Sso-7d from *Sulfolobus sulfataricus* or binds to antibodies generated against a native Archaeal small basic DNA-binding protein.

"Catalytic nucleic-acid-modifying domains having a processive nature" refers to a protein sequence or subsequence that performs as an enzyme having the ability to slide along the length of a nucleic acid molecule and chemically alter its structure repeatedly. A catalytic domain can include an entire enzyme, a subsequence thereof, or can include additional amino acid sequences that are not attached to the enzyme or subsequence as found in nature.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Efficiency" in the context of a nucleic acid modifying enzyme of this invention refers to the ability of the enzyme to perform its catalytic function under specific reaction conditions. Typically, "efficiency" as defined herein is indicated by the amount of modified bases generated by the modifying enzyme per binding to a nucleic acid.

"Enhances" in the context of an enzyme refers to improving the activity of the enzyme, i.e., increasing the amount of product per unit enzyme per unit time.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Methylase" refers to an enzyme that can modify a nucleic acid by the addition of a methyl group to a nucleotide.

"Nuclease" refers to an enzyme capable of cleaving the phosphodiester bonds between nucleotide subunits of nucleic acids.

"Nucleic-acid-modifying enzyme" refers to an enzyme that covalently alters a nucleic acid.

"Polymerase" refers to an enzyme that performs template-directed synthesis of polynucleotides.

"Processivity" refers to the ability of a nucleic acid modifying enzyme to remain attached to the template or substrate and perform multiple modification reactions. Typically "processivity" refers to the ability to modify relatively long tracts of nucleic acid.

"Restriction Endonuclease" refers to any of a group of enzymes, produced by bacteria, that cleave molecules of DNA internally at specific base sequences.

"Sequence-non-specific nucleic-acid-binding domain" refers to a protein domain which binds with significant affinity to a nucleic acid, for which there is no known nucleic acid which binds to the protein domain with more than 100-fold more affinity than another nucleic acid with the same nucleotide composition but a different nucleotide sequence.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus*, *Thermus brockianus*, and *Thermus thermophilus*; any recombinant enzymes deriving from *Thermus* species, and any functional derivatives thereof, whether derived by genetic modification or chemical modification or other methods known in the art.

BRIEF DESCRIPTION OF THE FIGURES

FIG. 1A: PCR amplification with a 22 nt forward primer; FIG. 1B: PCR amplification with a 15 nt primer; FIG. 1C: PCR amplification with a 12 nt primer.

DETAILED DESCRIPTION OF THE INVENTION

Figure 1A:
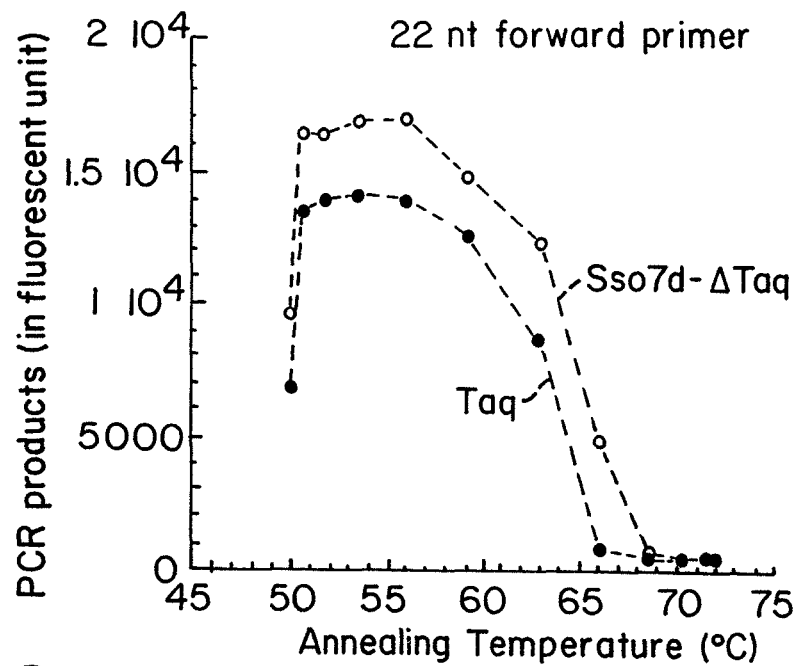
FIGS. 1A, 1B and 1C show the results of PCR amplification reactions performed using primers of different lengths to compare the efficiency of Sso7d-modified polymerase with the unmodified full-length polymerase.

The present invention is the discovery that sequence-non-specific double-stranded nucleic acid binding proteins can be joined to catalytic nucleic acid modifying proteins to enhance the processive nature of the catalytic protein. While the prior art taught that nucleic acid binding proteins can increase the binding affinity of enzymes to nucleic acid, the group of binding proteins having the ability to enhance the processive nature of the enzymes is of particular value. Not to be bound by theory, binding domains of the invention typically dissociate from double-stranded nucleic acid at a very slow rate. Thus, they increase the processivity and/or efficiency of a modifying enzyme to which they are joined by stabilizing the enzyme-nucleic acid complex. Accordingly, this invention includes the discovery that DNA-binding domains can stabilize the double-stranded conformation of a nucleic acid and increase the efficiency of a catalytic domain that requires a double-stranded substrate. Described herein are examples and simple assays to readily determine the improvement to the catalytic and/or processive nature of catalytic nucleic acid modifying enzymes.

Catalytic Nucleic-Acid-Modifying Domain

A catalytic nucleic-acid-modifying domain is the region of a modification enzyme that performs the enzymatic function. The catalytic nucleic-acid modifying domains of the invention can be processive, e.g., polymerase, exonuclease, etc., or non-processive, e.g., ligases, restriction endonucleases, etc.

Processivity reflects the ability of a nucleic acid modifying enzyme to synthesize or perform multiple modifications, e.g., nucleotide additions or methylations, in a single binding event. The processive proteins of the present invention exhibit enhanced processivity due to the presence of a sequence-non-specific double-stranded DNA binding domain that is joined to the processive modifying enzyme (or the enzymatic domain of the modifying enzyme), thereby providing a tethering domain to stabilize the nucleic acid/enzyme complex. Often the binding domain is from a thermostable organism and provides enhanced activity at higher temperatures, e.g., temperatures above 45° C. Examples of processive modifying enzymes include DNA polymerases, RNA polymerases, reverse transcriptases, methylases, 3' or 5' exonucleases, gyrases, and topoisomerase.

DNA Polymerases are well-known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases $\alpha$, $\delta$, and $\epsilon$, are implicated in nuclear replication, and a family A polymerase, polymerase $\gamma$, is used for mitochondrial DNA replication. Other types of DNA polymerases include phage polymerases.

Similarly, RNA polymerase typically include eukaryotic RNA polymerases I, II, and III, and bacterial RNA polymerases as well as phage and viral polymerases. RNA polymerases can be DNA-dependent and RNA-dependent.

Typically, DNA gyrases and topoisomerases play a role in higher orders of DNA structures such as supercoiling. DNA gyrases introduce negative supercoils. In prokaryotes, the A subunit is responsible for DNA cutting and reunion and the B subunit contains the ATP-hydrolysis activity. DNA gyrase introduces supercoiling processively and catalytically, typically introducing up to 100 supercoils per minute per molecule of DNA gyrase. In the absence of ATP, gyrase will slowly relax negative supercoils.

Topoisomerases are enzymes found in both prokaryotes and eukaryotes that catalyze the interconversion of different topological isomers of DNA, thereby causing a change in the link number. Topoisomerases can remove negative or positive supercoils from DNA or can introduce negative supercoils.

A variety of methylases and 3' or 5' exonucleases are also described in the art including bacterial, prokaryotic, eukaryotic and phage enzymes. Typically, exonucleases, such as lambda exonuclease, and some methylases are also processive.

The activity of a catalytic subunit can be measured using assays well known to those of skill in the art. For example, a processive enzymatic activity, such as a polymerase activity, can be measured by determining the amount of nucleic acid synthesized in a reaction, such as a polymerase chain reaction. In determining the relative efficiency of the enzyme, the amount of product obtained with a modifying enzyme of the invention, e.g. a polymerase containing a sequence-non-specific double-stranded DNA binding domain, can then be compared to the amount of product obtained with the normal modifying enzyme, which will be described in more detail below and in the Examples.

Modifying enzymes such as ligases or restriction endonucleases bind to double-stranded nucleic acids to perform the modifying function. The catalytic activity is typically measured by determining the amount of modified product produced under particular assay conditions. For example, ligase activity can be assayed by determining the amount of circularized plasmid, which had previously been digested with a restriction endonuclease to generate compatible ends, in a ligation reaction following incubation by quantifying the number of transformants obtained with an aliquot of the ligation reaction. Activity of a restriction endonuclease can be determined by assaying the extent of digestion of the target DNA, for example, by analyzing the extent of digestion of the DNA on a gel.

A catalytic modifying domain suitable for use in the invention can be the modifying enzyme itself or the catalytic modifying domain, e.g., Taq polymerase or a domain of Taq with polymerase activity. The catalytic domain may include additional amino acids and/or may be a variant that contains amino acid substitutions, deletions or additions, but still retains enzymatic activity.

Sequence-Non-Specific Nucleic-Acid-Binding Domain

A double-stranded sequence-non-specific nucleic acid binding domain is a protein or defined region of a protein that binds to double-stranded nucleic acid in a sequence-independent manner, i.e., binding does not exhibit a gross preference for a particular sequence. Typically, double-stranded nucleic acid binding proteins exhibit a 10-fold or higher affinity for double-stranded versus single-stranded nucleic acids. The double-stranded nucleic acid binding proteins in particular embodiments of the invention are preferably thermostable. Examples of such proteins include, but are not limited to, the Archaeal small basic DNA binding proteins Sac7d and Sso7d (see, e.g., Choli et al., *Biochimica et Biophysica Acta* 950: 193-203, 1988; Baumann et al., *Structural Biol.* 1:808-819, 1994; and Gao et al, *Nature Struc. Biol.* 5:782-786, 1998), Archael HMf-like proteins (see, e.g., Starich et al., *J. Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell:* 99, 155-166, 1999; De Felice et al., *J. Molec. Biol.* 291, 47-57, 1999; and Zhang et al., *Biochemistry* 34:10703-10712, 1995). Sso7d and Sac7d Sso7d and Sac7d are small (about 7,000 kd MW), basic chromosomal proteins from the hyperthermophilic archaeabacteria *Sulfolobus solfataricus* and *S. acidocaldarius*, respectively. These proteins are lysine-rich and have high thermal, acid and chemical stability. They bind DNA in a sequence-independent manner and when bound, increase the $T_M$ of DNA by up to 40° C. under some conditions (McAfee et al., *Biochemistry* 34:10063-10077, 1995). These proteins and their homologs are typically believed to be involved in stabilizing genomic DNA at elevated temperatures.

HMF-Like Proteins

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

PCNA Homologs

Many but not all family B DNA polymerases interact with accessory proteins to achieve highly processive DNA synthesis. A particularly important class of accessory proteins is referred to as the sliding clamp. Several characterized sliding clamps exist as trimers in solution, and can form a ring-like structure with a central passage capable of accommodating double-stranded DNA. The sliding clamp forms specific interactions with the amino acids located at the C terminus of particular DNA polymerases, and tethers those polymerases to the DNA template during replication. The sliding clamp in eukarya is referred to as the proliferating cell nuclear antigen (PCNA), while similar proteins in other domains are often referred to as PCNA homologs. These homologs have marked structural similarity but limited sequence similarity.

Recently, PCNA homologs have been identified from thermophilic Archaea (e.g., *Sulfalobus sofataricus*, *Pyroccocus furiosus*, etc.). Some family B polymerases in Archaea have a C terminus containing a consensus PCNA-interacting amino acid sequence and are capable of using a PCNA homolog as a processivity factor (see, e.g., Cann et al., *J. Bacteriol.* 181: 6591-6599, 1999 and De Felice et al., *J. Mol. Biol.* 291:47-57, 1999). These PCNA homologs are useful sequence-non-specific double-stranded DNA binding domains for the invention. For example, a consensus PCNA-interacting sequence can be joined to a polymerase that does not naturally interact with a PCNA homolog, thereby allowing a PCNA homolog to serve as a processivity factor for the polymerase. By way of illustration, the PCNA-interacting sequence from *Pyrococcus furiosus* PolII (a heterodimeric DNA polymerase containing two family B-like polypeptides) can be covalently joined to *Pyrococcus furiosus* PolI (a monomeric family B polymerase that does not normally interact with a PCNA homolog). The resulting fusion protein can then be allowed to associate non-covalently with the *Pyrococcus furiosus* PCNA homolog to generate a novel heterologous protein with increased processivity relative to the unmodified *Pyrococcus furiosus* PolI.

Other Sequence-Nonspecific Double-Stranded Nucleic Acid Binding Domains

Additional nucleic acid binding domains suitable for use in the invention can be identified by homology with known sequence non-specific double-stranded DNA binding proteins and/or by antibody crossreactivity, or may be found by means of a biochemical assay.

Identification of Nucleic Acid Binding Domains Based on Homology.

Typically, domains that have about 50% amino acid sequence identity, optionally about 60%, 75, 80, 85, 90, or 95-98% amino acid sequence identity to a known sequence non-specific double-stranded nucleic acid binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the following sequence comparison algorithms or by manual alignment and visual inspection. For purposes of this patent, percent amino acid identity is determined by the default parameters of BLAST.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One example of a useful algorithm is PILEUP. PILEUP creates a multiple sequence alignment from a group of related sequences using progressive, pair-wise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pair-wise alignment of the two most similar sequences, producing a cluster of two aligned sequences. This cluster is then aligned to the next most related sequence or cluster of aligned sequences. Two clusters of sequences are aligned by a simple extension of the pair-wise alignment of two individual sequences. The final alignment is achieved by a series of progressive, pair-wise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Cross-reactive Binding to Antibodies

Sequence non-specific doubled-stranded nucleic acid binding domains for use in the invention can also be identified by cross-reactivity using antibodies, preferably polyclonal antibodies, that bind to known nucleic acid binding domains. Polyclonal antibodies are generated using methods well known to those of ordinary skill in the art (see, e.g., Coligan, *Current Protocols in Immunology* (1991); Harlow & Lane, *Antibodies, A Laboratory Manual* (1988)). Those proteins that are immunologically cross-reactive binding proteins can then be detected by a variety of assay methods. For descriptions of various formats and conditions that can be used, see, e.g., *Methods in Cell Biology: Antibodies in Cell Biology*, volume 37 (Asai, ed. 1993), Coligan, supra, and Harlow & Lane, supra.

Useful immunoassay formats include assays where a sample protein is immobilized to a solid support. For example, a cross-reactive binding protein can be identified using an immunoblot analysis such as a western blot. The western blot technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that bind to the sequence non-specific double-stranded nucleic acid binding domain. The antibodies specifically bind to cross-reactive polypeptides on the solid support. The antibodies may be directly labeled or alternatively may be subsequently detected using labeled antibodies (e.g., labeled sheep anti-mouse antibodies) that specifically bind to the anti-binding domain antibodies. Other immunoblot assays, such as analysis of recombinant protein libraries, are also useful for identifying proteins suitable for use in the invention.

Using this methodology under designated immunoassay conditions, immunologically cross-reactive proteins that bind to a particular antibody at least two times the background or more, typically more than 10 times background, and do not substantially bind in a significant amount to other proteins present in the sample can be identified.

Immunoassays in the competitive binding format can also be used for crossreactivity determinations. For example, polyclonal antisera are generated to a known, sequence non-specific double-stranded nucleic acid binding domain protein, e.g., a *Pyrococcus furiosus* (Pfu) PCNA. The target antigen can then be immobilized to a solid support. Non-target antigens having minor crossreactivity (if they exist) can be added to the assay to improve the selectivity of the sera. The ability of the added proteins to compete for binding of the antisera to the immobilized protein is compared to the ability of the binding domain protein, in this example Pfu PCNA, to compete with itself. The percent crossreactivity for the above proteins is calculated, using standard calculations. Those antisera with less than 10% crossreactivity with the added protein are selected and pooled. Cross-reacting antibodies to non-target antigens can also be removed from the pooled antisera by immunoabsorption with the non-target antigens. Antibodies that specifically bind to particular nucleic acid binding domains of the invention can also be made using this methodology.

The immunoabsorbed and pooled antisera are then used in a competitive binding immunoassay as described above to compare a second protein, thought to be perhaps an allele, polymorphic variant or a homolog of the known binding domain, for example, a PCNA homolog from another *Pyrococcus* sp., to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the nucleic acid binding domain protein that is required to inhibit 50% of binding, then the second protein is said to specifically bind to the polyclonal antibodies generated to the nucleic acid binding domain immunogen.

Assays for Sequence Non-specific Double-stranded Nucleic Acid Binding Activity

The activity of the sequence non-specific double-stranded nucleic acid binding domains can be assessed using a variety of assays. Suitable binding domains exhibit a marked preference for double-stranded vs. single-stranded nucleic acids.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radio-labeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain suitable for use in the invention binds to double-stranded nucleic acids in a sequence-independent fashion, i.e., a binding domain of the invention binds double-stranded nucleic acids with a significant affinity, but, there is no known nucleic acid that binds to the domain with more than 100-fold more affinity than another nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific double-stranded nucleic acid binding domains for use in the invention can also be assessed, for example, by assaying the ability of the double-stranded binding domain to increase processivity or efficiency of a modifying enzyme or to increase the stability of a nucleic acid duplex by at least 1° C. can be determined. These techniques are discussed below in the section describing the analysis for enhanced efficiency of a nucleic acid modifying enzyme.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_M$ of the double-stranded substrate can be determined from the midpoint of the melting curve. The effect of the sequence-non-specific double-stranded nucleic-acid-binding protein on the $T_M$ can then be determined by comparing the $T_M$ obtained in the presence of the modified enzyme with that in the presence of the unmodified enzyme. (The protein does not significantly contribute to the UV absorbance because it has a much lower extinction coefficient at 260 nm than DNA). A domain that increases the $T_M$ by 1°, often by 5°, 10° or more, can then be selected for use in the invention.

Novel sequence non-specific double-stranded nucleic acid binding proteins of the invention can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

Joining the Catalytic Domain with the Nucleic-Acid-Binding Domain

The catalytic domain and the double-stranded nucleic-acid-binding domain can be joined by methods well known to those of skill in the art. These methods include chemical and recombinant means.

Chemical means of joining the heterologous domains are described, e.g., in *Bioconjugate Techniques*, Hermanson, Ed., Academic Press (1996). These include, for example, derivitization for the purpose of linking the moieties to each other, either directly or through a linking compound, by methods that are well known in the art of protein chemistry. For example, in one chemical conjugation embodiment, the means of linking the catalytic domain and the nucleic acid binding domain comprises a heterobifunctional coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The means of linking the heterologous domains of the protein may also comprise a peptidyl bond formed between moieties that are separately synthesized by standard peptide synthesis chemistry or recombinant means. The protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) *J. Am. Chem. Soc.*, 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, *Proteins Structures and Molecular Principles*, 50-60 (1983)). The composition of the synthetic polypeptides or of subfragments of the polypeptide, may be confirmed by amino acid analysis or sequencing (e.g., the Edman degradation procedure; see Creighton, *Proteins, Structures and Molecular Principles*, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In another embodiment, the domains of a protein of the invention, e.g., Sso7d and Taq polymerase, are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

In a specific embodiment, the coding sequences of each polypeptide in the fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Val and Thr residues. Other near neutral amino acids, such as Ser and Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have nonessential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Other methods of joining the domains include ionic binding by expressing negative and positive tails and indirect binding through antibodies and streptavidin-biotin interactions. (See, e.g., *Bioconjugate Techniques*, supra). The domains may also be joined together through an intermediate interacting sequence. For example, a consensus PCNA-interacting sequence can be joined to a polymerase that does not naturally interact with a PCNA homolog. The resulting fusion protein can then be allowed to associate non-covalently with the PCNA homolog to generate a novel heterologous protein with increased processivity.

Production of Fusion Proteins Using Recombinant Techniques

In one embodiment, a protein of the invention is produced by recombinant expression of a nucleic acid encoding the protein, which is well known to those of skill in the art. Such a fusion product can be made by ligating the appropriate nucleic acid sequences encoding the desired amino acid sequences to each other by methods known in the art, in the proper coding frame, and expressing the product by methods known in the art.

Nucleic acids encoding the domains to be incorporated into the fusion proteins of the invention can be obtained using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Often, the nucleic acid sequences encoding catalytic or nucleic acid binding domains or related nucleic acid sequence homologs are cloned from cDNA and genomic DNA libraries by hybridization with probes, or isolated using amplification techniques with oligonucleotide primers. Amplification techniques can be used to amplify and isolate sequences from DNA or RNA (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes.

In an example of obtaining a nucleic acid encoding a catalytic or nucleic acid binding domain using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Other physical properties of a polypeptide expressed from a particular nucleic acid can be compared to properties of known sequence nonspecific double-stranded nucleic acid binding proteins or nucleic acid modifying enzyme catalytic domains to provide another method of identifying suitable nucleic acids.

In some embodiments, it may be desirable to modify the polypeptides encoding the catalytic and/or nucleic acid binding regions of the recombinant fusion protein. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

For example, the catalytic and/or nucleic acid binding domains can be modified to facilitate the linkage of the two domains to obtain the polynucleotides that encode the fusion polypeptides of the invention. Catalytic domains and binding domains that are modified by such methods are also part of the invention. For example, a codon for a cysteine residue can be placed at either end of a domain so that the domain can be linked by, for example, a sulfide linkage. The modification can be performed using either recombinant or chemical methods (see, e.g., Pierce Chemical Co. catalog, Rockford Ill.).

The catalytic and binding domains of the recombinant fusion protein are often joined by linker domains, usually polypeptide sequences such as those described above, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In some embodiments, the recombinant nucleic acids encoding the proteins of the invention are modified to provide preferred codons which enhance translation of the nucleic acid in a selected organism (e.g., yeast preferred codons are substituted into a coding nucleic acid for expression in yeast).

Expression Cassettes and Host Cells for Expressing the Fusion Polypeptides

There are many expression systems for producing the fusion polypeptide that are well know to those of ordinary skill in the art. (See, e.g., *Gene Expression Systems, Fernandex and Hoeffler, Eds. Academic Press,* 1999.) Typically, the polynucleotide that encodes the fusion polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res*. (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, and fusion expression systems such as GST and LacZ. Epitope tags can also be added to recombinant proteins to provide convenient methods of isolation, e.g., c-myc, HA-tag, 6-His tag (SEQ ID NO:13), maltose binding protein, VSV-G tag, anti-DYKDDDDK tag (SEQ ID NO:14), or any such tag, a large number of which are well known to those of skill in the art.

For expression of fusion polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol*.; Tabor et al. (1985) *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification*., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

One of skill would recognize that modifications could be made to the catalytic and sequence nonspecific double-stranded nucleic acid binding domains without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

Assays to Determine Improved Activity for the Catalytic Domains.

Activity of the catalytic domain can be measured using a variety of assays that can be used to compare processivity or modification activity of a modifying protein domain joined to a binding domain compared to the protein by itself. Improvement in activity includes both increased processivity and increased efficiency.

Improved Activity of Processive Modifying Enzymes

Polymerase processivity can be measured in variety of methods known to those of ordinary skill in the art. Polymerase processivity is generally defined as the number of nucleotides incorporated during a single binding event of a modifying enzyme to a primed template.

For example, a 5' FAM-labeled primer is annealed to circular or linearized ssM13 mp18 DNA to form a primed template. In measuring processivity, the primed template usually is present in significant molar excess to the enzyme or catalytic domain to be assayed so that the chance of any primed template being extended more than once by the polymerase is minimized. The primed template is therefore mixed with the polymerase catalytic domain to be assayed at a ratio such as approximately 4000:1 (primed DNA:DNA polymerase) in the presence of buffer and dNTPs. $MgCl_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a protein of the invention, i.e., a protein that contains a sequence non-specific double-stranded nucleic acid binding domain fused to the catalytic domain of a processive nucleic acid modifying enzyme such as a polymerase, is then compared to the processivity of the enzyme without the binding domain.

Enhanced efficiency can also be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12 nucleotide in length, primer annealed at an elevated temperature, e.g., 50° C. In this analysis, enhanced efficiency is shown by the ability of a polymerase such as a Taq polymerase to produce more product in a PCR reaction using the 12 nucleotide primer annealed at 50° C. when it is joined to a sequence-non-specific double-stranded nucleic-acid-binding domain of the invention, e.g., Sso7d, than Taq polymerase does alone. In contrast, a binding tract that is a series of charged residues, e.g. lysines, when joined to a polymerase does not enhance processivity.

Similar assay conditions can be employed to test for improved processivity when the catalytic domain is a reverse transcriptase, methylase, gyrase, topoisomerase, or an exonuclease. In these analyses, processivity is measured as the ability of the enzyme to remain attached to the template or substrate and perform multiple modification reactions. The molar ratio of nucleic acid to enzyme is typically sufficiently high so that one the average only one enzyme molecule is bound per substrate nucleic acid. For example, the activity of a processive exonuclease, lambda exonuclease, can be assayed using published methods (see, e.g., Mitsis and Kwagh, *Nucleic Acid Research*, 27:3057-3063, 1999). In brief, a long DNA substrates (0.5-20 kb) can be amplified from a DNA template using a 5'-biotinylated primer as the forward primer and a 5' phosphorylated primer as the reverse primer, or vice versa. Radio-labeled dATP is used to internally label the PCR fragment, which serves as the substrate for the lambda exonuclease. The purified internally-labeled substrate is mixed with the enzyme at a sufficient high molar ratio of DNA to enzyme to ensure that on average only one exonuclease molecule bound per substrate DNA. Aliquots of the sample are removed over time and can be assayed either by gel electrophoresis or by monitoring the formation of acid soluble radio-labels.

Enhanced Activity of Non-processive Modifying Enzymes

Catalytic domains of non-processive DNA modifying enzymes, or the enzymes themselves, can also be used in the invention. Examples of such modifying enzymes include ligases and restriction endonucleases. Often, the catalytic domains are obtained from thermostable *Thermus* or *Pyrococcus* species. To determine improved activity, the enzymatic function can be analyzed under a variety of conditions, often increased reaction temperatures, e.g., temperatures 45° C. or above, and compared to the unmodified enzyme activity.

For example, Taq DNA ligase catalyzes the formation of a phosphodiester bond between juxtaposed 5' phosphate and 3' hydroxyl termini of two adjacent oligonucleotides that are hybridized to a complementary target DNA. The enzyme is active at 45° C.-65° C. The yield of the ligated product is dependent on how efficiently the complementary strands of DNA are annealed to form the substrate for the enzyme. A binding domain of the invention, such as a Sso7d-like protein, when joined to the ligase can stabilize the DNA duplex by increasing its melting temperature, so that an elevated reaction temperature can be used to maximize the activity of the enzyme without compromising the basepairing interactions.

The effect of Sso7d fusion on the activity of a ligase can be analyzed by comparing the ligation efficiency of the modified versus that of the unmodified enzyme. The ligation efficiency of two linear DNA fragments can be monitored by agarose gel electrophoresis, whereas the ligation efficiency of converting a linearized plasmid to a circular plasmid can be monitored by DNA transformation.

In another example, the catalytic domain of a nucleic acid modifying enzyme with improved activity can be from a restriction enzyme isolated from a thermophilic species that requires an elevated reaction temperature to achieve optimal activity. For example when the restriction enzyme recognition sites are located very close to the end of a DNA fragment or in duplexed oligonucleotides, higher temperatures may destabilize the duplex structure. At a higher reaction temperature, e.g., 45° C. or above, a restriction enzyme with improved activity because of the presence of a binding domain of the invention, e.g., an Sso7d-like protein joined to the restriction endonuclease, can produce a greater amount of product, i.e., digested DNA, than the restriction enzyme by itself. The product yield from a particular reaction can be assessed by visualization on a gel or by assessment of transformation efficiency.

Other methods of assessing enhanced efficiency of the improved nucleic acid modifying enzymes of the invention can be determined by those of ordinary skill in the art using standard assays of the enzymatic activity of a given modification enzyme. Thus, processive modifying enzymes such as reverse transcriptases, methylases, gyrases, and topoisomerases, and other non-processive modifying enzymes can be similarly analyzed by comparing activities of the protein, or a catalytic domain, joined to a sequence non-specific double-stranded nucleic acid binding domain and the protein by itself.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of non-critical parameters that could be changed or modified to yield essentially similar results.

Example 1

Construction of Fusion Proteins

Construction of Sso7d-ΔTaq Fusion.

The following example illustrates the construction of a polymerase protein possessing enhanced processivity, in which the sequence-non-specific double-stranded nucleic acid binding protein Sso7d is fused to the *Thermus aquaticus* PolI DNA polymerase (a family A polymerase known as Taq DNA polymerase) that is deleted at the N terminus by 289 amino acids (ΔTaq).

Based on the published amino acid sequence of Sso7d, seven oligonucleotides were used in constructing a synthetic gene encoding Sso7d. The oligonucleotides were annealed and ligated using T4 DNA ligase. The final ligated product was used as the template in a PCR reaction using two terminal oligonucleotides as primers to amplify the full-length gene. By design, the resulting PCR fragment contains a unique EcoRI site at the 5' terminus, and a unique BstXI site at the 3' terminus. In addition to encoding the Sso7d protein, the above PCR fragment also encodes a peptide linker with the amino acid sequence of Gly-Gly-Val-Thr (SEQ ID NO:15) positioned at the C terminus of the Sso7d protein. The synthetic gene of Sso7d has the DNA sequence shown in SEQ ID NO:1, and it encodes a polypeptide with the amino acid sequence shown in SEQ ID NO:2.

The synthetic gene encoding Sso7d was then used to generate a fusion protein in which Sso7d replaces the first 289 amino acid of Taq. The fragment encoding Sso7d was subcloned into a plasmid encoding Taq polymerase to generate the fusion protein, as follows. Briefly, the DNA fragment containing the synthetic Sso7d gene was digested with restriction endonucleases EcoRI and BstXI, and ligated into the corresponding sites of a plasmid encoding Taq. As the result, the region that encodes the first 289 amino acid of Taq is replaced by the synthetic gene of Sso7d. This plasmid (pYW1) allows the expression of a single polypeptide containing Sso7d fused to the N terminus of ΔTaq via a synthetic linker composed of Gly-Gly-Val-Thr (SEQ ID NO:15). The DNA sequence encoding the fusion protein (Sso7d-ΔTaq) and the amino acid sequence of the protein are shown in SEQ ID NOs:3 and 4, respectively.

Construction of Sso 7d-Taq Fusion.

An Sso7d/full-length Taq fusion protein was also constructed. Briefly, a 1 kb PCR fragment encoding the first 336 amino acids of Taq polymerase was generated using two primers. The 5' primer introduces a SpeI site into the 5' terminus of the PCR fragment, and the 3' primer hybridizes to nucleotides 1008-1026 of the Taq gene. The fragment was digested with SpeI and BstXI, releasing a 0.9 kb fragment encoding the first 289 amino acids of Taq polymerase. The 0.9 kb fragment was ligated into plasmid pYW1 at the SpeI (located in the region encoding the linker) and BstXI sites. The resulting plasmid (pYW2) allows the expression of a single polypeptide containing the Sso7d protein fused to the N terminus of the full length Taq DNA polymerase via a linker composed of Gly-Gly-Val-Thr, the same as in Sso7d-ΔTaq. The DNA sequence encoding the Sso7d-Taq fusion protein and the amino acid sequence of the protein are shown in SEQ ID NOs. 5 and 6, respectively.

Construction of Pfu-Sso7d Fusion.

A third fusion protein was created, joining Sso7d to the C terminus of *Pyrococcus furiosus* DNA polI (a family B DNA polymerase known as Pfu). A pET-based plasmid carrying the Pfu DNA polymerase gene was modified so that a unique KpnI site and a unique SpeI site are introduced at the 3' end of the Pfu gene before the stop codon. The resulting plasmid (pPFKS) expresses a Pfu polymerase with three additional amino acids (Gly-Thr-His) at its C terminus.

Two primers were used to PCR amplify the synthetic Sso7d gene described above to introduce a Kpn I site and a NheI site flanking the Sso7d gene. The 5' primer also introduced six additional amino acids (Gly-Thr-Gly-Gly-Gly-Gly; SEQ ID NO:16), which serve as a linker, at the N terminus of the Sso7d protein. Upon digestion with KpnI and NheI, the PCR fragment was ligated into pPFKS at the corresponding sites. The resulting plasmid (pPFS) allows the expression of a single polypeptide containing Sso7d protein fused to the C terminus of the Pfu polymerase via a peptide linker (Gly-Thr-Gly-Gly-Gly-Gly; SEQ ID NO:16). The DNA sequence encoding the fusion protein (Pfu-Sso7d) and the amino acid sequence of the fusion protein are shown in SEQ ID NOs: 7 and 8, respectively.

Construction of Sac7d-ΔTaq Fusion.

A fourth fusion protein was constructed, which joined a sequence-non-specific DNA binding protein from a different species to ΔTaq. Two primers were used to PCR amplify the Sac7d gene from genomic DNA of *Sulfolobus acidocaldarius*. The primers introduced a unique EcoRI site and a unique SpeI site to the PCR fragment at the 5' and 3' termini, respectively. Upon restriction digestion with EcoRI and SpeI, the PCR fragment was ligated into pYW1 (described above) at the corresponding sites. The resulting plasmid expresses a single polypeptide containing the Sac7d protein fused to the N terminus of ΔTaq via the same linker as used in Sso7d-ΔTaq. The DNA sequence of the fusion protein (Sac7d-ΔTaq) and the amino acid sequence of the protein are shown in SEQ ID. NOs: 9 and 10, respectively.

Construction of PL-ΔTaq Fusion.

A fifth fusion protein joins a peptide composed of 14 lysines and 2 arginines to the N terminus of ΔTaq. To generate the polylysine (PL)-ΔTaq fusion protein, two 67 nt oligonucleotides were annealed to form a duplexed DNA fragment with a 5' protruding end compatible with an EcoRI site, and a 3' protruding end compatible with an SpeI site. The DNA fragment encodes a lysine-rich peptide of the following composition: NSKKKKKKKRKKRKKKGGGVT (SEQ ID NO:17). The numbers of lysines and arginines in this peptide are identical to the that in Sso7d. This DNA fragment was ligated into pYW1, predigested with EcoRI and SpeI, to replace the region encoding Sso7d. The resulting plasmid (pLST) expresses a single polypeptide containing the lysine-rich peptide fused to the N terminus of ΔTaq. The DNA sequence encoding the fusion protein (PL-ΔTaq) and the amino acid sequence of the protein are shown in SEQ ID NOs: 11 and 12, respectively.

Example 2

Assessing the Processivity of the Fusion Polymerases

This example illustrates enhancement of processivity of the fusion proteins of the invention generated in Example 1.

Polymerase Unit Definition Assay

The following assay was used to define a polymerase unit. An oligonucleotide was pre-annealed to ssM13mp 18 DNA in the presence of $Mg^{++}$-free reaction buffer and dNTPs. The DNA polymerase of interest was added to the primed DNA mixture. $MgCl_2$ was added to initiate DNA synthesis at 72° C. Samples were taken at various time points and added to TE buffer containing PicoGreen (Molecular Probes, Eugene Oreg.). The amount of DNA synthesized was quantified using a fluorescence plate reader. The unit activity of the DNA polymerase of interest was determined by comparing its initial rate with that of a control DNA polymerase (e.g., a commercial polymerase of known unit concentration).

Processivity Assay

Processivity was measured by determining the number of nucleotides incorporated during a single binding event of the polymerase to a primed template.

Briefly, 40 nM of a 5' FAM-labeled primer (34 nt long) was annealed to 80 nM of circular or linearized ssM13mp18 DNA to form the primed template. The primed template was mixed with the DNA polymerase of interest at a molar ratio of approximately 4000:1 (primed DNA:DNA polymerase) in the presence of standard PCR buffer (free of $Mg^{++}$) and 200 µM of each dNTPs. $MgCl_2$ was added to a final concentration of 2 mM to initiate DNA synthesis. At various times after initiation, samples were quenched with sequencing loading dye containing 99% formamide, and analyzed on a sequencing gel. The median product length, which is defined as the product length above or below which there are equal amounts of products, was determined based on integration of all detectable product peaks. At a polymerase concentration for which the median product length change with time or polymerase concentration, the length corresponds to the processivity of the enzyme. The ranges presented in Table 1 represent the range of values obtained in several repeats of the assay.

TABLE I

Comparison of processivity

| DNA polymerase | Median product length (nt) |
|---|---|
| ΔTaq | 2-6 |
| Sso7d-ΔTaq | 39-58 |
| PL-ΔTaq | 2-6 |
| Taq | 15-20 |
| Sso7d-Taq | 130-160 |
| Pfu | 2-3 |
| Pfu-Sso7d | 35-39 |

In comparing the processivity of modified enzyme to the unmodified enzyme, ΔTaq had a processivity of 2-6 nucleotides, whereas Sso7d-ΔTaq fusion exhibited a processivity of 39-58 nucleotides (Table I). Full length Taq had a processivity of 15-20 nucleotides, which was significantly lower than that of Sso7d-Taq fusion with a processivity of 130-160 nucleotides. These results demonstrate that Sso7d joined to Taq polymerase enhanced the processivity of the polymerase.

Pfu belongs to family B of polymerases. Unlike Taq polymerase, Pfu possesses a 3' to 5' exonuclease activity, allowing it to maintain high fidelity during DNA synthesis. A modified Pfu polymerase, in which Sso7d is fused to the C terminus of the full length Pfu polymerase, and an unmodified Pfu polymerase were analyzed in the processivity assay described above. As shown in Table I, the Pfu polymerase exhibited a processivity of 2-3 nt, whereas the Pfu-Sso7d fusion protein had a processivity of 35-39 nt. Thus, the fusion of Sso7d to the C terminus of Pfu resulted in a >10-fold enhancement of the processivity over the unmodified enzyme.

The ability of a lysine-rich peptide to enhance the processivity of Taq polymerase was also assessed. The processivity of PL-ΔTaq was measured using the method described above, and compared to that of the unmodified protein, ΔTaq. As shown in Table I, the presence of the polylysine tract did not enhance the processivity of ΔTaq. Thus, although the addition of a lysine-rich peptide to a nucleic acid binding protein may increase the association rate of an enzyme to its substrate as disclosed in the prior art, processivity is not increased.

Example 3

Effect of Fusion Proteins on Oligonucleotide Annealing Temperature

This experiment demonstrates the increased efficiency of the Sso7d-ΔTaq fusion protein, compared to Taq, to produce product at higher annealing temperatures by stabilizing dsDNA.

Two primers, primer 1008 (19mer; $T_M$=56.4° C.) and 2180R (20mer; $T_M$=56.9° C.), were used to amplify a 1 kb fragment (1008-2180) of the Taq pol gene. A gradient thermal cycler (MJ Research, Waltham Mass.) was used to vary the annealing temperature from 50° C. to 72° C. in a PCR cycling program. The amounts of PCR products generated using identical number of units of Sso7d-ΔTaq and Taq were quantified and compared. The results are shown in Table II. The Sso7d-ΔTaq fusion protein exhibited significantly higher efficiency than full length Taq at higher annealing temperatures. Thus, the presence of Sso7d in cis increases the melting temperature of the primer on the template.

The annealing temperature assay above was used to investigate whether PL-ΔTaq has any effect on the annealing temperature of primer during PCR amplification. As shown in Table II, little or no amplified product was observed when the annealing temperature was at or above 63° C.

TABLE II

Comparison of activities at different annealing temperatures.

| Polymerase | Activity at 63° C. | Activity at 66° C. | Activity at 69° C. |
|---|---|---|---|
| Taq | 85% | 30% | <10% |
| Sso7d-ΔTaq | >95% | 70% | 40% |
| PL-ΔTaq | <5% | nd | nd | nd: not detectable.

Example 4

Effect of Fusion Proteins on Required Primer Length

An enhancement of $T_M$ of the primers (as shown above) predicts that shorter primers could be used by Sso7d-ΔTaq, but not by Taq, to achieve efficient PCR amplification. This analysis shows that Sso7d-ΔTaq is more efficient in an assay using shorter primers compared to Taq.

Figure 1B:
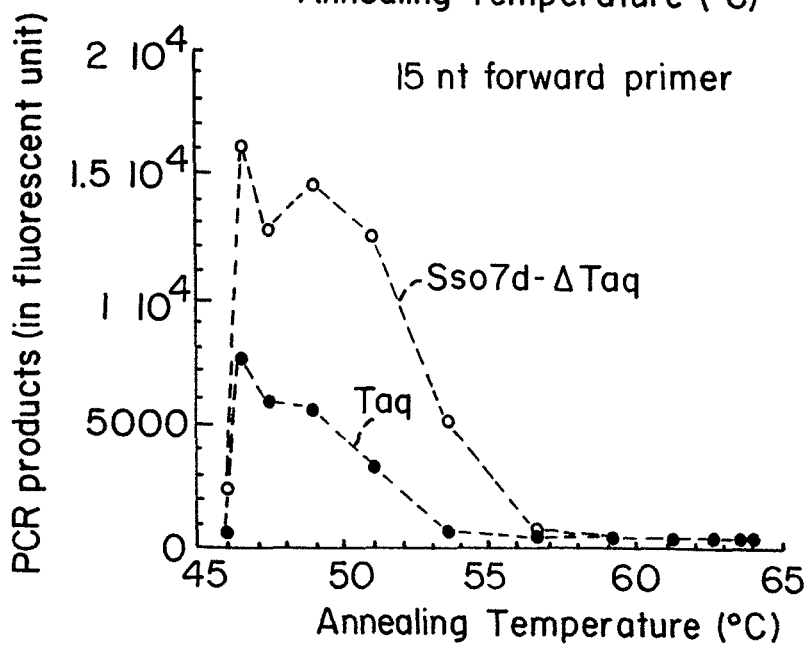
Figure 1C:
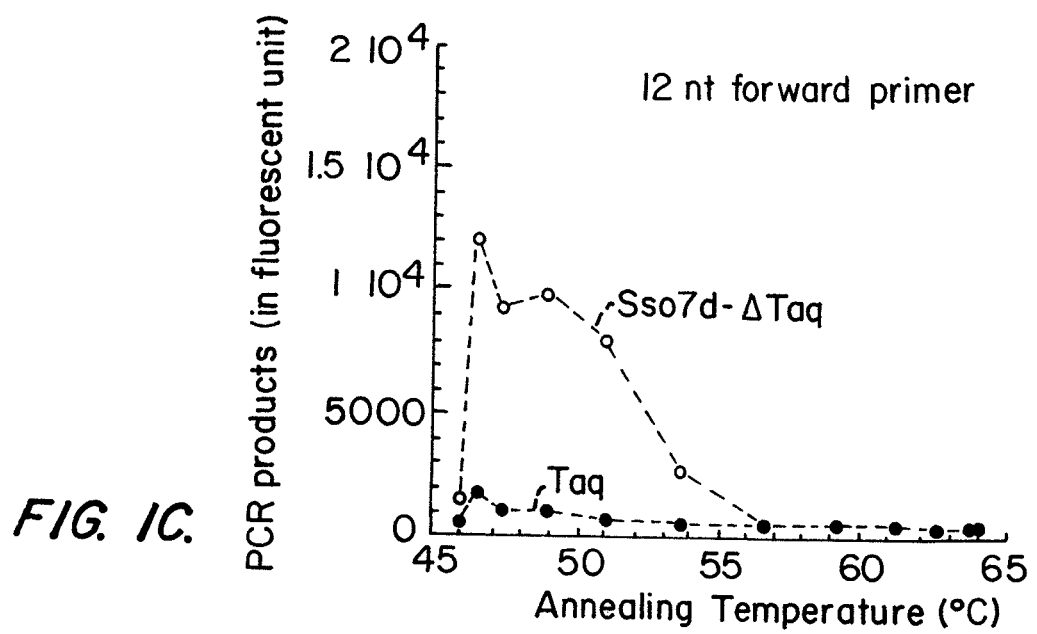

Primers of different lengths were used to compare the efficiencies of PCR amplification by Sso7d-ΔTaq and by Taq. The results are shown in Table III and in FIG. 1A-1C. When two long primers, 57F (22mer, $T_M$=58° C.) and 732R (24mer, $T_M$=57° C.) were used, no significant difference was observed between Sso7d-ΔTaq and Taq at either low or high annealing temperatures. When medium length primers, 57F15 (15mer, $T_M$=35° C.) and 732R16 (16mer, $T_m$=35° C.), were used, Sso7d-ΔTaq was more efficient than Taq, especially when the annealing temperature was high. The most striking difference between the two enzymes was observed with short primers, 57F12 (12mer) and 732R16 (16mer), where Sso7d-ΔTaq generated 10 times more products than Taq at both low and high annealing temperatures.

Figure 2:
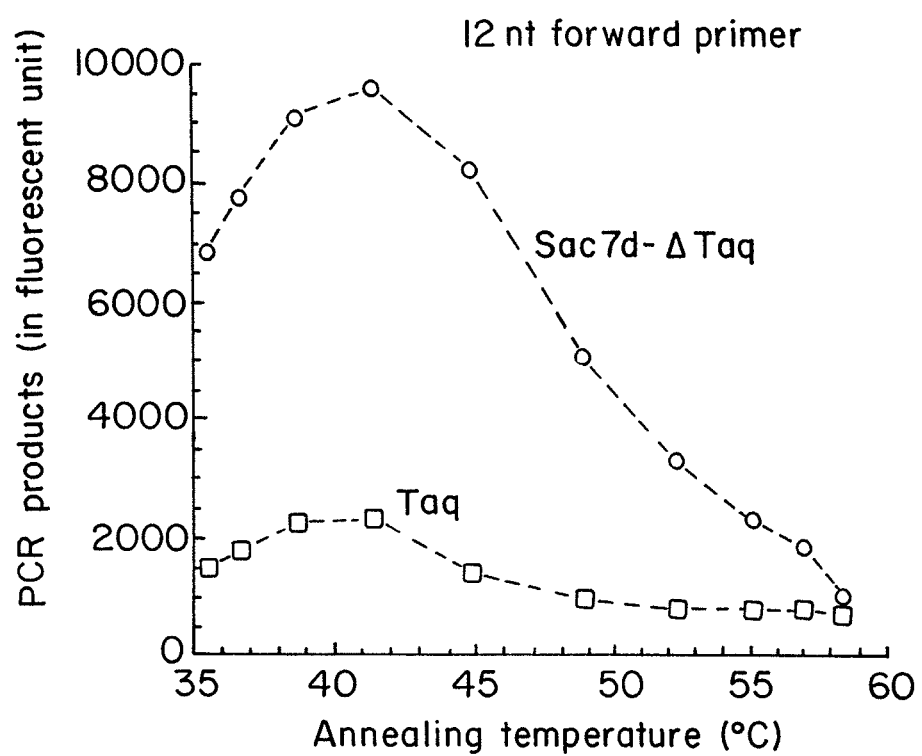
FIG. 2 shows the results of a PCR amplification reaction using a 12 nt forward primer to evaluate the PCR products generated using Sac7d-ΔTaq compared to Taq.

PCR using primers 57F12 (12 nt) and 732R16 (16 nt) were used to compare the efficiency of Sac7d-ΔTaq to the unmodified full length Taq in PCR reaction. Results are shown in FIG. 2. Similar to Sso7d-ΔTaq, Sac7d-ΔTaq is significantly more efficient than Taq in amplifying using short primers.

A primer length assay was used to determine the ability of PL-ΔTaq to use short primers in PCR amplification. When long primers (57F and 732R) were used, the amplified product generated by PL-ΔTaq is ~50% of that by Sso7d-ΔTaq. When short primers (57F12 and 732R16) were used, the amplified product generated by PL-ΔTaq is <20% of that by Sso7d-ΔTaq.

TABLE III

Comparison of the effect of primer length on PCR amplification by Sso7d-ΔTaq and Taq DNA polymerase.

| | 22 nt primer | | 15 nt primer | | 12 nt primer | |
|---|---|---|---|---|---|---|
| polymerase | Anneal @55° C. | Anneal @63° C. | Anneal @49° C. | Anneal @54° C. | Anneal @49° C. | Anneal @54° C. |
| Taq | 14000 | 9000 | 5500 | <500 | 1000 | undetectable |
| Sso7d-ΔTaq | 17000 | 13000 | 15000 | 5000 | 10000 | 3000 |
| Sso7d-ΔTaq:Taq | 1.2:1 | 1.4:1 | 2.7:1 | >10:1 | 10:1 | >10:1 |

Listing of Sequences

SEQ ID NO: 1
Synthetic Sso7d gene
GCAACCGTAAAGTTCAAGTACAAAGGCGAAGAAAAAGAGGTAGACATCTC

CAAGATCAAGAAAGTATGGCGTGTGGGCAAGATGATCTCCTTCACCTACG

ACGAGGGCGGTGGCAAGACCGGCCGTGGTGCGGTAAGCGAAAAGGACGCG

CCGAAGGAGCTGCTGCAGATGCTGGAGAAGCAGAAAAAG

SEQ ID NO: 2
The amino acid sequence of Sso7d.
ATVKFKYKGEEKEVDISKIKKVWRVGKMISFTYDEGGGKTGRGAVSEKDA

PKELLQMLEKQKK

SEQ ID NO: 3
The DNA sequence encoding the Sso7d-ΔTaq fusion protein
ATGATTACGAATTCGAGCGCAACCGTAAAGTTCAAGTACAAAGGCGAAGA

```
AAAAGAGGTAGACATCTCCAAGATCAAGAAAGTATGGCGTGTGGGCAAGA
TGATCTCCTTCACCTACGACGAGGGCGGTGGCAAGACCGGCCGTGGTGCG
GTAAGCGAAAAGGACGCGCCGAAGGAGCTGCTGCAGATGCTGGAGAAGCA
GAAAAAGGGCGGCGGTGTCACTAGTCCCAAGGCCCTGGAGGAGGCCCCCT
GGCCCCCGCCGGAAGGGGCCTTCGTGGGCTTTGTGCTTTCCCGCAAGGAG
CCCATGTGGGCCGATCTTCTGGCCCTGGCCGCCGCCAGGGGGGCCGGGT
CCACCGGGCCCCCGAGCCTTATAAAGCCCTCAGGGACCTGAAGGAGGCGC
GGGGGCTTCTCGCCAAAGACCTGAGCGTTCTGGCCCTGAGGGAAGGCCTT
GGCCTCCCGCCCGGCGACGACCCCATGCTCCTCGCCTACCTCCTGGACCC
TTCCAACACCACCCCCGAGGGGGTGGCCCGGCGCTACGGCGGGGAGTGGA
CGGAGGAGGCGGGGAGCGGGCCGCCCTTTCCGAGAGGCTCTTCGCCAAC
CTGTGGGGGAGGCTTGAGGGGGAGGAGAGGCTCCTTTGGCTTTACCGGGA
GGTGGAGAGGCCCCTTTCCGCTGTCCTGGCCCACATGGAGGCCACGGGGG
TGCGCCTGGACGTGGCCTATCTCAGGGCCTTGTCCCTGGAGGTGGCCGAG
GAGATCGCCCGCCTCGAGGCCGAGGTCTTCCGCCTGGCCGGCCACCCCTT
CAACCTCAACTCCCGGGACCAGCTGGAAAGGGTCCTCTTTGACGAGCTAG
GCTTCCCGCCATCGGCAAGACGGAGAAGACCGGCAAGCGCTCCACCAGC
GCCGCCGTCCTGGAGGCCCTCCGCGAGGCCCACCCCATCGTGGAGAAGAT
CCTGCAGTACCGGGAGCTCACCAAGCTGAAGAGCACCTACATTGACCCCT
TGCCGGACCTCATCCACCCCAGGACGGGCCGCCTCCACACCCGCTTCAAC
CAGACGGCCACGGCCACGGGCAGGCTAAGTAGCTCCGATCCCAACCTCCA
GAACATCCCCGTCCGCACCCCGCTTGGGCAGAGGATCCGCCGGGCCTTCA
TCGCCGAGGAGGGGTGGCTATTGTGGCCCTGGACTATAGCCAGATAGAG
CTCAGGGTGCTGGCCCACCTCTCCGGCGACGAGAACCTGATCCGGGTCTT
CCAGGAGGGGCGGGACATCCACACGGAGACCGCCAGCTGGATGTTCGGCG
TCCCCCGGGAGGCCGTGGACCCCCTGATGCGCCGGGCGGCCAAGACCATC
AACTTCGGGGTCCTCTACGGCATGTCGGCCCACCGCCTCTCCCAGGAGCT
AGCCATCCCTTACGAGGAGGCCCAGGCCTTCATTGAGCGCTACTTTCAGA
GCTTCCCCAAGGTGCGGGCCTGGATTGAGAAGACCCTGGAGGAGGGCAGG
AGGCGGGGTACGTGGAGACCCTCTTCGGCCGCCGCCGCTACGTGCCAGA
CCTAGAGGCCCGGGTGAAGAGCGTGCGGGAGGCGGCCGAGCGCATGGCCT
TCAACATGCCCGTCCAGGGCACCGCCGCCGACCTCATGAAGCTGGCTATG
GTGAAGCTCTTCCCCAGGCTGGAGGAAATGGGGGCCAGGATGCTCCTTCA
GGTCCACGACGAGCTGGTCCTCGAGGCCCCAAAAGAGAGGGCGGAGGCCG
TGGCCCGGCTGGCCAAGGAGGTCATGGAGGGGGTGTATCCCCTGGCCGTG
CCCCTGGAGGTGGAGGTGGGGATAGGGGAGGACTGGCTCTCCGCCAAGGA
GGGCATTGATGGCCGCGGCGGAGGCGGGCATCATCATCATCATCATTAA
                                        SEQ ID NO: 4
The amino acid sequence of Sso7d-ΔTaq fusion
protein
MITNSSATVKFKYKGEEKEVDISKIKKVWRVGKMISFTYDEGGGKTGRGA
VSEKDAPKELLQMLEKQKKGGGVTSPKALEEAPWPPPEGAFVGFVLSRKE
PMWADLLALAAARGGRVHRAPEPYKALRDLKEARGLLAKDLSVLALREGL
GLPPGDDPMLLAYLLDPSNTTPEGVARRYGGEWTEEAGERAALSERLFAN
LWGRLEGEERLLWLYREVERPLSAVLAHMEATGVRLDVAYLRALSLEVAE
EIARLEAEVFRLAGHPFNLNSRDQLERVLFDELGLPAIGKTEKTGKRSTS
AAVLEALREAHPIVEKILQYRELTKLKSTYIDPLPDLIHPRTGRLHTRFN
QTATATGRLSSSDPNLQNIPVRTPLGQRIRRAFIAEEGWLLVALDYSQIE
LRVLAHLSGDENLIRVFQEGRDIHTETASWMFGVPREAVDPLMRRAAKTI
NFGVLYGMSAHRLSQELAIPYEEAQAFIERYFQSFPKVRAWIEKTLEEGR
RRGYVETLFGRRRYVPDLEARVKSVREAAERMAFNMPVQGTAADLMKLAM
VKLFPRLEEMGARMLLQVHDELVLEAPKERAEAVARLAKEVMEGVYPLAV
PLEVEVGIGEDWLSAKEGIDRGGGGHHHHHH
                                        SEQ ID NO: 5
The DNA sequence encoding the Sso7d-Taq fusion
protein
ATGATTACGAATTCGAGCGCAACCGTAAAGTTCAAGTACAAAGGCGAAGA
AAAAGAGGTAGACATCTCCAAGATCAAGAAAGTATGGCGTGTGGGCAAGA
TGATCTCCTTCACCTACGACGAGGGCGGTGGCAAGACCGGCCGTGGTGCG
GTAAGCGAAAAGGACGCGCCGAAGGAGCTGCTGCAGATGCTGGAGAAGCA
GAAAAAGGGCGGCGGTGTCACTAGTGGGATGCTGCCCCTCTTTGAGCCCA
AGGGCCGGGTCCTCCTGGTGGACGGCCACCACCTGGCCTACCGCACCTTC
CACGCCCTGAAGGGCCTCACCACCAGCCGGGGGGAGCCGGTGCAGGCGGT
CTACGGCTTCGCCAAGAGCCTCCTCAAGGCCCTCAAGGAGGACGGGACG
CGGTGATCGTGGTCTTTGACGCCAAGGCCCCCTCCTTCCGCCACGAGGCC
TACGGGGGGTACAAGGCGGGCCGGGCCCCCACGCAGAGGACTTTCCCCG
GCAACTCGCCCTCATCAAGGAGCTGGTGGACCTCCTGGGGCTGGCGCGCC
TCGAGGTCCCGGGCTACGAGGCGGACGACGTCCTGGCCAGCCTGGCCAAG
AAGGCGGAAAAGGAGGGCTACGAGGTCCGCATCCTCACCGCCGACAAAGA
CCTTTACCAGCTCCTTTCCGACCGCATCCACGTCCTCCACCCCGAGGGGT
ACCTCATCACCCCGGCCTGGCTTTGGGAAAAGTACGGCCTGAGGCCCGAC
CAGTGGGCCGACTACCGGGCCCTGACCGGGGACGAGTCCGACAACCTTCC
CGGGGTCAAGGGCATCGGGGAGAAGACGGCGAGGAAGCTTCTGGAGGAGT
GGGGGAGCCTGGAAGCCCTCCTCAAGAACCTGGACCGGCTGAAGCCCGCC
ATCCGGGAGAAGATCCTGGCCCACATGGACGATCTGAAGCTCTCCTGGGA
CCTGGCCAAGGTGCGCACCGACCTGCCCCTGGAGGTGGACTTCGCCAAAA
GGCGGGAGCCCGACCGGGAGAGGCTTAGGGCCTTTCTGGAGAGGCTTGAG
TTTGGCAGCCTCCTCCACGAGTTCGGCCTTCTGGAAAAGCCCCAAGGCCT
GGAGGAGGCCCCTGGCCCCCGCCGGAAGGGGCCTTCGTGGGCTTTGTGC
TTTCCCGCAAGGAGCCCATGTGGGCCGATCTTCTGGCCCTGGCCGCCGCC
AGGGGGGGCCGGGTCCACCGGGCCCCCGAGCCTTATAAAGCCCTCAGGGA
CCTGAAGGAGGCGCGGGGGCTTCTCGCCAAAGACCTGAGCGTTCTGGCCC
TGAGGGAAGGCCTTGGCCTCCCGCCCGGCGACGACCCCATGCTCCTCGCC
TACCTCCTGGACCCTTCCAACACCACCCCCGAGGGGGTGGCCCGGCGCTA
```

```
CGGCGGGGAGTGGACGGAGGAGGCGGGGGAGCGGGCCGCCCTTTCCGAGA
GGCTCTTCGCCAACCTGTGGGGGAGGCTTGAGGGGGAGGAGAGGCTCCTT
TGGCTTTACCGGGAGGTGGAGAGGCCCCTTTCCGCTGTCCTGGCCCACAT
GGAGGCCACGGGGGTGCGCCTGGACGTGGCCTATCTCAGGGGCTTGTCCC
TGGAGGTGGCCGAGGAGATCGCCCGCCTCGAGGCCGAGGTCTTCCGCCTG
GCCGGCCACCCCTTCAACCTCAACTCCCGGGACCAGCTGGAAAGGGTCCT
CTTTGACGAGCTAGGGCTTCCCGCCATCGGCAAGACGGAGAAGACCGGCA
AGCGCTCCACCAGCGCCGCCGTCCTGGAGGCCCTCCGCGAGGCCCACCCC
ATCGTGGAGAAGATCCTGCAGTACCGGGAGCTCACCAAGCTGAAGAGCAC
CTACATTGACCCCTTGCCGGACCTCATCCACCCCAGGACGGGCCGCCTCC
ACACCCGCTTCAACCAGACGGCCACGGCCACGGGCAGGCTAAGTAGCTCC
GATCCCAACCTCCAGAACATCCCCGTCCGCACCCCGCTTGGGCAGAGGAT
CCGCCGGGCCTTCATCGCCGAGGAGGGGTGGCTATTGGTGGCCCTGGACT
ATAGCCAGATAGAGCTCAGGGTGCTGGCCCACCTCTCCGGCGACGAGAAC
CTGATCCGGGTCTTCCAGGAGGGGCGGGACATCCACACGGAGACCGCCAG
CTGGATGTTCGGCGTCCCCCGGGAGGCCGTGGACCCCCTGATGCGCCGGG
CGGCCAAGACCATCAACTTCGGGGTCCTCTACGGCATGTCGGCCCACCGC
CTCTCCCAGGAGCTAGCCATCCCTTACGAGGAGGCCCAGGCCTTCATTGA
GCGCTACTTTCAGAGCTTCCCCAAGGTGCGGGCCTGGATTGAGAAGACCC
TGGAGGAGGGCAGGAGGCGGGGGTACGTGGAGACCCTCTTCGGCCGCCGC
CGCTACGTGCCAGACCTAGAGGCCCGGGTGAAGAGCGTGCGGGAGGCGGC
CGAGCGCATGGCCTTCAACATGCCCGTCCAGGGCACCGCCGCCGACCTCA
TGAAGCTGGCTATGGTGAAGCTCTTCCCCAGGCTGGAGGAAATGGGGGCC
AGGATGCTCCTTCAGGTCCACGACGAGCTGGTCCTCGAGGCCCCAAAAGA
GAGGGCGGAGGCCGTGGCCCGGCTGGCCAAGGAGGTCATGGAGGGGGTGT
ATCCCCTGGCCGTGCCCCTGGAGGTGGAGGTGGGGATAGGGGAGGACTGG
CTCTCCGCCAAGGAGGGCATTGATGGCCGCGGCGGAGGCGGGCATCATCA
TCATCATCATTAA
                                      SEQ ID NO: 6
The amino acid sequence of Sso7d-Taq fusion
protein.
MITNSSATVKFKYKGEEKEVDISKIKKVWRVGKMISFTYDEGGGKTGRGA
VSEKDAPKELLQMLEKQKKGGGVTSGMLPLFEPKGRVLLVDGHHLAYRTF
HALKGLTTSRGEPVQAVYGFAKSLLKALKEDGDAVIVVFDAKAPSFRHEA
YGGYKAGRAPTPEDFPRQLALIKELVDLLGLARLEVPGYEADDVLASLAK
KAEKEGYEVRILTADKDLYQLLSDRIHVLHPEGYLITPAWLWEKYGLRPD
QWADYRALTGDESDNLPGVKGIGEKTARKLLEEWGSLEALLKNLDRLKPA
IREKILAHMDDLKLSWDLAKVRTDLPLEVDFAKRREPDRERLRAFLERLE
FGSLLHEFGLLESPKALEEAPWPPPEGAFVGFVLSRKEPMWADLLALAAA
RGGRVHRAPEPYKALRDLKEARGLLAKDLSVLALREGLGLPPGDDPMLLA
YLLDPSNTTPEGVARRYGGEWTEEAGERAALSERLFANLWGRLEGEERLL
WLYREVERPLSAVLAHMEATGVRLDVAYLRALSLEVAEEIARLEAEVFRL
AGHPFNLNSRDQLERVLFDELGLPAIGKTEKTGKRSTSAAVLEALREAHP
IVEKILQYRELTKLKSTYIDPLPDLIHPRTGRLHTRFNQTATATGRLSSS
DPNLQNIPVRTPLGQRIRRAFIAEEGWLLVALDYSQIELRVLAHLSGDEN
LIRVFQEGRDIHTETASWMFGVPREAVDPLMRRAAKTINFGVLYGMSAHR
LSQELAIPYEEAQAFIERYFQSFPKVRAWIEKTLEEGRRRGYVETLFGRR
RYVPDLEARVKSVREAAERMAFNMPVQGTAADLMKLAMVKLFPRLEEMGA
RMLLQVHDELVLEAPKERAEAVARLAKEVMEGVYPLAVPLEVEVGIGEDW
LSAKEGIDRGGGGHHHHHH
                                      SEQ ID NO: 7
The DNA sequence encoding the Pfu-Sso7d fusion
protein
ATGATTTTAGATGTGGATTACATAACTGAAGAAGGAAAACCTGTTATTAG
GCTATTCAAAAAAGAGAACGGAAAATTTAAGATAGAGCATGATAGAACTT
TTAGACCATACATTTACGCTCTTCTCAGGGATGATTCAAAGATTGAAGAA
GTTAAGAAAATAACGGGGGAAAGGCATGGAAAGATTGTGAGAATTGTTGA
TGTAGAGAAGGTTGAGAAAAAGTTTCTCGGCAAGCCTATTACCGTGTGGA
AACTTTATTTGGAACATCCCCAAGATGTTCCCACTATTAGAGAAAAAGTT
AGAGAACATCCAGCAGTTGTGGACATCTTCGAATACGATATTCCATTTGC
AAAGAGATACCTCATCGACAAAGGCCTAATACCAATGGAGGGGGAAGAAG
AGCTAAAGATTCTTGCCTTCGATATAGAAACCCTCTATCACGAAGGAGAA
GAGTTTGGAAAAGGCCCAATTATAATGATTAGTTATGCAGATGAAAATGA
AGCAAAGGTGATTACTTGGAAAAACATAGATCTTCCATACGTTGAGGTTG
TATCAAGCGAGAGAGAGATGATAAAGAGATTTCTCAGGATTATCAGGGAG
AAGGATCCTGACATTATAGTTACTTATAATGGAGACTCATTCGACTTCCC
ATATTTAGCGAAAAGGGCAGAAAAACTTGGGATTAAATTAACCATTGGAA
GAGATGGAAGCGAGCCCAAGATGCAGAGAATAGGCGATATGACGGCTGTA
GAAGTCAAGGGAAGAATACATTTCGACTTGTATCATGTAATAACAAGGAC
AATAAATCTCCCAACATACACACTAGAGGCTGTATATGAAGCAATTTTTG
GAAAGCCAAAGGAGAAGGTATACGCCGACGAGATAGCAAAGGCCTGGGAA
AGTGGAGAGAACCTTGAGAGAGTTGCCAAATACTCGATGGAAGATGCAAA
GGCAACTTATGAACTCGGGAAAGAATTCCTTCCAATGGAAATTCAGCTTT
CAAGATTAGTTGGACAACCTTTATGGGATGTTTCAAGGTCAAGCACAGGG
AACCTTGTAGAGTGGTTCTTACTTAGGAAAGCCTACGAAAGAAACGAAGT
AGCTCCAAACAAGCCAAGTGAAGAGGAGTATCAAAGAAGGCTCAGGGAGA
GCTACACAGGTGGATTCGTTAAAGAGCCAGAAAAGGGGTTGTGGGAAAAC
ATAGTATACCTAGATTTTAGAGCCCTATATCCCTCGATTATAATTACCCA
CAATGTTTCTCCCGATACTCTAAATCTTGAGGGATGCAAGAACTATGATA
TCGCTCCTCAAGTAGGCCACAAGTTCTGCAAGGACATCCCTGGTTTTATA
CCAAGTCTCTTGGGACATTTGTTAGAGGAAAGACAAAAGATTAAGACAAA
AATGAAGGAAACTCAAGATCCTATAGAAAAAATACTCCTTGACTATAGAC
AAAAAGCGATAAAACTCTTAGCAAATTCTTTCTACGGATATTATGGCTAT
GCAAAAGCAAGATGGTACTGTAAGGAGTGTGCTGAGAGCGTTACTGCCTG
```

-continued
```
GGGAAGAAAGTACATCGAGTTAGTATGGAAGGAGCTCGAAGAAAAGTTTG
GATTTAAAGTCCTCTACATTGACACTGATGGTCTCTATGCAACTATCCCA
GGAGGAGAAAGTGAGGAAATAAAGAAAAAGGCTCTAGAATTTGTAAAATA
CATAAATTCAAAGCTCCCTGGACTGCTAGAGCTTGAATATGAAGGGTTTT
ATAAGAGGGGATTCTTCGTTACGAAGAAGAGGTATGCAGTAATAGATGAA
GAAGGAAAAGTCATTACTCGTGGTTTAGAGATAGTTAGGAGAGATTGGAG
TGAAATTGCAAAAGAAACTCAAGCTAGAGTTTTGGAGACAATACTAAAAC
ACGGAGATGTTGAAGAAGCTGTGAGAATAGTAAAAGAAGTAATACAAAAG
CTTGCCAATTATGAAATTCCACCAGAGAAGCTCGCAATATATGAGCAGAT
AACAAGACCATTACATGAGTATAAGGCGATAGGTCCTCACGTAGCTGTTG
CAAAGAAACTAGCTGCTAAAGGAGTTAAAATAAAGCCAGGAATGGTAATT
GGATACATAGTACTTAGAGGCGATGGTCCAATTAGCAATAGGGCAATTCT
AGCTGAGGAATACGATCCCAAAAAGCACAAGTATGACGCAGAATATTACA
TTGAGAACCAGGTTCTTCCAGCGGTACTTAGGATATTGGAGGGATTTGGA
TACAGAAAGGAAGACCTCAGATACCAAAAGACAAGACAAGTCGGCCTAAC
TTCCTGGCTTAACATTAAAAAATCCGGTACCGGCGGTGGCGGTGCAACCG
TAAAGTTCAAGTACAAAGGCGAAGAAAAAGAGGTAGACATCTCCAAGATC
AAGAAAGTATGGCGTGTGGGCAAGATGATCTCCTTCACCTACGACGAGG
CGGTGGCAAGACCGGCCGTGGTGCGGTAAGCGAAAAGGACGCGCCGAAGG
AGCTGCTGCAGATGCTGGAGAAGCAGAAAAAGTGA
```

SEQ ID NO: 8
The amino acid sequence of the Pfu-Sso7d fusion protein
```
MILDVDYITEEGKPVIRLFKKENGKFKIEHDRTFRPYIYALLRDDSKIEE
VKKITGERHGKIVRIVDVEKVEKKFLGKPITVWKLYLEHPQDVPTIREKV
REHPAVVDIFEYDIPFAKRYLIDKGLIPMEGEEELKILAFDIETLYHEGE
EFGKGPIIMISYADENEAKVITWKNIDLPYVEVVSSEREMIKRFLRIIRE
KDPDIIVTYNGDSFDFPYLAKRAEKLGIKLTIGRDGSEPKMQRIGDMTAV
EVKGRIHFDLYHVITRTINLPTYTLEAVYEAIFGKPKEKVYADEIAKAWE
SGENLERVAKYSMEDAKATYELGKEFLPMEIQLSRLVGQPLWDVSRSSTG
NLVEWFLLRKAYERNEVAPNKPSEEEYQRRLRESYTGGFVKEPEKGLWEN
IVYLDFRALYPSIIITHNVSPDTLNLEGCKNYDIAPQVGHKFCKDIPGFI
PSLLGHLLEERQKIKTKMKETQDPIEKILLDYRQKAIKLLANSFYGYYGY
AKARWYCKECAESVTAWGRKYIELVWKELEEKFGFKVLYIDTDGLYATIP
GGESEEIKKKALEFVKYINSKLPGLLELEYEGFYKRGFFVTKKRYAVIDE
EGKVITRGLEIVRRDWSEIAKETQARVLETILKHGDVEEAVRIVKEVIQK
LANYEIPPEKLAIYEQITRPLHEYKAIGPHVAVAKKLAAKGVKIKPGMVI
GYIVLRGDGPISNRAILAEEYDPKKHKYDAEYYIENQVLPAVLRILEGFG
YRKEDLRYQKTRQVGLTSWLNIKKSGTGGGGATVKFKYKGEEKEVDISKI
KKVWRVGKMISFTYDEGGGKTGRGAVSEKDAPKELLQMLEKQKK
```

SEQ ID NO: 9
The DNA sequence encoding the Sac7d-ΔTaq fusion protein

```
ATGATTACGAATTCGACGGTGAAGGTAAAGTTCAAGTATAAGGGTGAAGA
GAAAGAAGTAGACACTTCAAAGATAAAGAAGGTTTGGAGAGTAGGCAAAA
TGGTGTCCTTTACCTATGACGACAATGGTAAGACAGGTAGAGGAGCTGTA
AGCGAGAAAGATGCTCCAAAAGAATTATTAGACATGTTAGCAAGAGCAGA
AAGAGAGAAGAAAGGCGGCGGTGTCACTAGTCCCAAGGCCCTGGAGGAGG
CCCCCTGGCCCCCGCCGGAAGGGGCCTTCGTGGGCTTTGTGCTTTCCCGC
AAGGAGCCCATGTGGGCCGATCTTCTGGCCCTGGCCGCCGCCAGGGGGGG
CCGGGTCCACCGGGCCCCCGAGCCTTATAAAGCCCTCAGGGACCTGAAGG
AGGCGCGGGGCTTCTCGCCAAAGACCTGAGCGTTCTGGCCCTGAGGGAA
GGCCTTGGCCTCCCGCCCGGCGACGACCCCATGCTCCTCGCCTACCTCCT
GGACCCTTCCAACACCACCCCCGAGGGGGTGGCCCGGCTACGGCGGGG
AGTGGACGGAGGAGGCGGGGGAGCGGGCCGCCCTTTCCGAGAGGCTCTTC
GCCAACCTGTGGGGAGGCTTGAGGGGAGGAGAGGCTCCTTTGGCTTTA
CCGGGAGGTGGAGAGGCCCCTTTCCGCTGTCCTGGCCCACATGGAGGCCA
CGGGGGTGCGCCTGGACGTGGCCTATCTCAGGGCCTTGTCCCTGGAGGTG
GCCGAGGAGATCGCCCGCCTCGAGGCCGGGTCTTCCGCCTGGCCGGCCAC
CCCTTCAACCTCAACTCCCGGGACCAGCTGGAAAGGGTCCTCTTTGACGA
GCTAGGGCTTCCCGCCATCGGCAAGACGGAGAAGACCGGCAAGCGCTCCA
CCAGCGCCGCCGTCCTGGAGGCCCTCCGCGAGGCCCACCCCATCGTGGAG
AAGATCCTGCAGTACCGGGAGCTCACCAAGCTGAAGAGCACCTACATTGA
CCCCTTGCCGGACCTCATCCACCCCAGGACGGGCCGCCTCCACACCCGCT
TCAACCAGACGGCCACGGCCACGGGCAGGCTAAGTAGCTCCGATCCCAAC
CTCCAGAACATCCCCGTCCGCACCCCGCTTGGGCAGAGGATCCGCCGGGC
CTTCATCGCCGAGGAGGGGTGGCTATTGGTGGCCCTGGACTATAGCCAGA
TAGAGCTCAGGGTGCTGGCCCACCTCTCCGGCGACGAGAACCTGATCCGG
GTCTTCCAGGAGGGGCGGGACATCCACACGGAGACCGCCAGCTGGATGTT
CGGCGTCCCCCGGGAGGCCGTGGACCCCCTGATGCGCCGGGCGGCCAAGA
CCATCAACTTCGGGGTCCTCTACGGCATGTCGGCCCACCGCCTCTCCCAG
GAGCTAGCCATCCCTTACGAGGAGGCCCAGGCCTTCATTGAGCGCTACTT
TCAGAGCTTCCCCAAGGTGCGGGCCTGGATTGAGAAGACCCTGGAGGAGG
GCAGGAGGCGGGGGTACGTGGAGACCCTCTTCGGCCGCCGCCGCTACGTG
CCAGACCTAGAGGCCCGGGTGAAGAGCGTGCGGGAGGCGGCCGAGCGCAT
GGCCTTCAACATGCCCGTCCAGGGCACCGCCGCCGACCTCATGAAGCTGG
CTATGGTGAAGCTCTTCCCCAGGCTGGAGGAAATGGGGGCCAGGATGCTC
CTTCAGGTCCACGACGAGCTGGTCCTCGAGGCCCCAAAAGAGAGGGCGGA
GGCCGTGGCCCGGCTGGCCAAGGAGGTCATGGAGGGGGTGTATCCCCTGG
CCGTGCCCCTGGAGGTGGAGGTGGGGATAGGGGAGGACTGGCTCTCCGCC
AAGGAGGGCATTGATGGCCGCGGCGGAGGCGGGCATCATCATCATCATCA
TTAA
```

SEQ ID NO: 10
The amino acid sequence of the Sac7d-ΔTaq fusion protein

MITNSTVKVKFKYKGEEKEVDTSKIKKVWRVGKMVSFTYDDNGKTGRGAV
SEKDAPKELLDMLARAEREKKGGGVTSPKALEEAPWPPPEGAFVGFVLSR
KEPMWADLLALAAARGGRVHRAPEPYKALRDLKEARGLLAKDLSVLALRE
GLGLPPGDDPMLLAYLLDPSNTTPEGVARRYGGEWTEEAGERAALSERLF
ANLWGRLEGEERLLWLYREVERPLSAVLAHMEATGVRLDVAYLRALSLEV
AEEIARLEAEVFRLAGHPFNLNSRDQLERVLFDELGLPAIGKTEKTGKRS
TSAAVLEALREAHPIVEKILQYRELTKLKSTYIDPLPDLIHPRTGRLHTR
FNQTATATGRLSSSDPNLQNIPVRTPLGQRIRRAFIAEEGWLLVALDYSQ
IELRVLAHLSGDENLIRVFQEGRDIHTETASWMFGVPREAVDPLMRRAAK
TINFGVLYGMSAHRLSQELAIPYEEAQAFIERYFQSFPKVRAWIEKTLEE
GRRRGYVETLFGRRRYVPDLEARVKSVREAAERMAFNMPVQGTAADLMKL
AMVKLFPRLEEMGARMLLQVHDELVLEAPKERAEAVARLAKEVMEGVYPL
AVPLEVEVGIGEDWLSAKEGIDGRGGGHHHHHH

SEQ ID NO: 11
The DNA sequence encoding the PL-ΔTaq fusion protein
ATGATTACGAATTCGAAGAAAAAGAAAAAGAAAAAGCGTAAGAAACGCAA
AAAGAAAAAGAAAGGCGGCGGTGTCACTAGTGGCGCAACCGTAAAGTTCA
AGTACAAAGGCGAAGAAAAAGAGGTAGACATCTCCAAGATCAAGAAAGTA
TGGCGTGTGGGCAAGATGATCTCCTTCACCTACGACGAGGGCGGTGGCAA
GACCGGCCGTGGTGCGGTAAGCGAAAAGGACGCGCCGAAGGAGCTGCTGC
AGATGCTGGAGAAGCAGAAAAAGGGCGGCGGTGTCACCAGTCCCAAGGCC
CTGGAGGAGGCCCCCTGGCCCCCGCCGGAAGGGGCCTTCGTGGGCTTTGT
GCTTTCCCGCAAGGAGCCCATGTGGGCCGATCTTCTGGCCCTGGCCGCCG
CCAGGGGGGGCCGGGTCCACCGGGCCCCCGAGCCTTATAAAGCCCTCAGG
GACCTGAAGGAGGCGCGGGGGCTTCTCGCCAAAGACCTGAGCGTTCTGGC
CCTGAGGGAAGGCCTTGGCCTCCCGCCCGGCGACGACCCCATGCTCCTCG
CCTACCTCCTGGACCCTTCCAACACCACCCCCGAGGGGGTGGCCCGGCGC
TACGGCGGGGAGTGGACGGAGGAGGCGGGGGAGCGGGCCGCCCTTTCCGA
GAGGCTCTTCGCCAACCTGTGGGGGAGGCTTGAGGGGGAGGAGAGGCTCC
TTTGGCTTTACCGGGAGGTGGAGAGGCCCCTTTCCGCTGTCCTGGCCCAC
ATGGAGGCCACGGGGGTGCGCCTGGACGTGGCCTATCTCAGGGCCTTGTC
CCTGGAGGTGGCCGAGGAGATCGCCCGCCTCGAGGCCGAGGTCTTCCGCC
TGGCCGGCCACCCCTTCAACCTCAACTCCCGGGACCAGCTGGAAAGGGTC
CTCTTTGACGAGCTAGGGCTTCCCGCCATCGGCAAGACGGAGAAGACCGG
CAAGCGCTCCACCAGCGCCGCCGTCCTGGAGGCCCTCCGCGAGGCCCACC CCATCGTGGAGAAGATCCTGCAGTACCGGGAGCTCACCAAGCTGAAGAGC
ACCTACATTGACCCCTTGCCGGACCTCATCCACCCCAGGACGGGCCGCCT
CCACACCCGCTTCAACCAGACGGCCACGGCCACGGGCAGGCTAAGTAGCT
CCGATCCCAACCTCCAGAACATCCCCGTCCGACACCCGCTTGGGCAGAGG
ATCCGCCGGGCCTTCATCGCCGAGGAGGGGTGGCTATTGGTGGCCCTGGA
CTATAGCCAGATAGAGCTCAGGGTGCTGGCCCACCTCTCCGGCGACGAGA
ACCTGATCCGGGTCTTCCAGGAGGGGCGGGACATCCACACGGAGACCGCC
AGCTGGATGTTCGGCGTCCCCCGGGAGGCCGTGGACCCCCTGATGCGCCG
GGCGGCCAAGACCATCAACTTCGGGGTCCTCTACGGCATGTCGGCCCACC
GCCTCTCCCAGGAGCTAGCCATCCCTTACGAGGAGGCCCAGGCCTTCATT
GAGCGCTACTTTCAGAGCTTCCCCAAGGTGCGGGCCTGGATTGAGAAGAC
CCTGGAGGAGGGCAGGAGGCGGGGGTACGTGGAGACCCTCTTCGGCCGCC
GCCGCTACGTGCCAGACCTAGAGGCCCGGGTGAAGAGCGTGCGGGAGGCG
GCCGAGCGCATGGCCTTCAACATGCCCGTCCAGGGCACCGCCGCCGACCT
CATGAAGCTGGCTATGGTGAAGCTCTTCCCCAGGCTGGAGGAAATGGGGG
CCAGGATGCTCCTTCAGGTCCACGACGAGCTGGTCCTCGAGGCCCCAAAA
GAGAGGGCGGAGGCCGTGGCCCGGCTGGCCAAGGAGGTCATGGAGGGGGT
GTATCCCCTGGCCGTGCCCCTGGAGGTGGAGGTGGGGATAGGGGAGGACT
GGCTCTCCGCCAAGGAGGGCATTGATGGCCGCGGCGGAGGCGGGCATCAT
CATCATCATCATTAA SEQ ID NO: 12
The amino acid sequence of PL-ΔTaq fusion protein
MITNSKKKKKKKRKKRKKKKKGGGVTSGATVKFKYKGEEKEVDISKIKKV
WRVGKMISFTYDEGGGKTGRGAVSEKDAPKELLQMLEKQKKGGGVTSPKA
LEEAPWPPPEGAFVGFVLSRKEPMWADLLALAAARGGRVHRAPEPYKALR
DLKEARGLLAKDLSVLALREGLGLPPGDDPMLLAYLLDPSNTTPEGVARR
YGGEWTEEAGERAALSERLFANLWGRLEGEERLLWLYREVERPLSAVLAH
MEATGVRLDVAYLRALSLEVAEEIARLEAEVFRLAGHPFNLNSRDQLERV
LFDELGLPAIGKTEKTGKRSTSAAVLEALREAHPIVEKILQYRELTKLKS
TYIDPLPDLIHPRTGRLHTRFNQTATATGRLSSSDPNLQNIPVRTPLGQR
IRRAFIAEEGWLLVALDYSQIELRVLAHLSGDENLIRVFQEGRDIHTETA
SWMFGVPREAVDPLMRRAAKTINFGVLYGMSAHRLSQELAIPYEEAQAFI
ERYFQSFPKVRAWIEKTLEEGRRRGYVETLFGRRRYVPDLEARVKSVREA
AERMAFNMPVQGTAADLMKLAMVKLFPRLEEMGARMLLQVHDELVLEAPK
ERAEAVARLAKEVMEGVYPLAVPLEVEVGIGEDWLSAKEGIDGRGGGHH
HHHH

What is claimed is

1. A method of synthesizing DNA from an RNA template, the method comprising contacting the RNA template with a primer and a polypeptide comprising a sequence non-specific double-stranded nucleic acid binding polypeptide that has at least 75% identity to SEQ ID NO:2 or amino acids 7-71 of SEQ ID NO:10 joined to reverse transcriptase; and incubating the solution under conditions where the primer is extended.

2. The method of claim 1, wherein the sequence non-specific double-stranded nucleic acid binding polypeptide comprises the amino acid sequence of SEQ ID NO:2 or amino acids 7-71 of SEQ ID NO:10.

3. The method of claim 1, wherein the sequence non-specific double-stranded nucleic acid binding polypeptide has at least 80% identity to SEQ ID NO:2.

4. The method of claim 1, wherein the sequence non-specific double-stranded nucleic acid binding polypeptide comprises SEQ ID NO:2.

5. A polypeptide comprising a sequence non-specific double-stranded nucleic acid binding polypeptide that has at least 75% identity to SEQ ID NO:2, or amino acids 7-71 of SEQ ID NO:10, joined to reverse transcriptase.

6. The polypeptide of claim 5, wherein the sequence non-specific double-stranded nucleic acid binding polypeptide comprises the amino acid sequence of SEQ ID NO:2 or amino acids 7-71 of SEQ ID NO:10.

7. The polypeptide of claim 5, wherein the sequence non-specific double-stranded nucleic acid binding polypeptide has at least 80% identity to SEQ ID NO:2.

8. The polypeptide of claim 5, wherein the sequence non-specific double-stranded nucleic acid binding polypeptide has at least 90% identity to SEQ ID NO:2.

9. The polypeptide of claim 5, wherein the sequence non-specific double-stranded nucleic acid binding polypeptide comprises the amino acid sequence of SEQ ID NO:2.

10. The polypeptide of claim 5, wherein the sequence non-specific double-stranded nucleic acid binding polypeptide has at least 80% identity to amino acids 7-71 of SEQ ID NO:10.

11. The polypeptide of claim 5, wherein the sequence non-specific double-stranded nucleic acid binding polypeptide has at least 90% identity to amino acids 7-71 of SEQ ID NO:10.

12. The polypeptide of claim 5, wherein the sequence non-specific double-stranded nucleic acid binding polypeptide comprises amino acids 7-71 of SEQ ID NO:10.

13. The method of claim 1, wherein the sequence non-specific double-stranded nucleic acid binding polypeptide has at least 90% identity to SEQ ID NO:2.

14. The method of claim 1, wherein the sequence non-specific double-stranded nucleic acid binding polypeptide has at least 80% identity to amino acids 7-71 of SEQ ID NO:10.

15. The method of claim 1, wherein the sequence non-specific double-stranded nucleic acid binding polypeptide has at least 90% identity to amino acids 7-71 of SEQ ID NO:10.

16. The method of claim 1, wherein the sequence non-specific double-stranded nucleic acid binding polypeptide comprises amino acids 7-71 of SEQ ID NO:10.

* * * * *